(12) United States Patent
Springer et al.

(10) Patent No.: US 9,580,482 B2
(45) Date of Patent: Feb. 28, 2017

(54) CONFORMATION-STABILIZED TRAP ANTIGENS

(71) Applicant: Children's Medical Center Corporation, Boston, MA (US)

(72) Inventors: Timothy A. Springer, Boston, MA (US); Chafen Lu, Chestnut Hill, MA (US); Gaojie Song, Boston, MA (US); Adem Koksal, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/379,050

(22) PCT Filed: Feb. 15, 2013

(86) PCT No.: PCT/US2013/026461
§ 371 (c)(1),
(2) Date: Aug. 15, 2014

(87) PCT Pub. No.: WO2013/123412
PCT Pub. Date: Aug. 22, 2013

(65) Prior Publication Data
US 2015/0147349 A1    May 28, 2015

Related U.S. Application Data

(60) Provisional application No. 61/600,570, filed on Feb. 17, 2012, provisional application No. 61/600,567, filed on Feb. 17, 2012.

(51) Int. Cl.
*A61K 39/015* (2006.01)
*A61K 39/002* (2006.01)
*C07K 14/445* (2006.01)
*A61K 39/00* (2006.01)

(52) U.S. Cl.
CPC .......... *C07K 14/445* (2013.01); *A61K 39/015* (2013.01); *A61K 2039/6075* (2013.01); *C07K 2319/21* (2013.01); *C07K 2319/43* (2013.01)

(58) Field of Classification Search
None
See application file for complete search history.

(56) References Cited

U.S. PATENT DOCUMENTS 5,811,106 A    9/1998    Robson et al.

FOREIGN PATENT DOCUMENTS

| WO | 91-11516 | 8/1991 |
| WO | 2008-009650 | 1/2008 |
| WO | 2009-059298 | 5/2009 |

OTHER PUBLICATIONS

International Search Report and Written Opinion for PCT/US2013/026461 dated Jun. 21, 2013.
Chenet et al., "Genetic diversity of vaccine candidate antigens in Plasmodium falciparum isolates from the Amazon basin of Peru", Malaria Journal (2008) vol. 7, Article No. 93.

*Primary Examiner* — Jennifer Graser
(74) *Attorney, Agent, or Firm* — Fish & Richardson P.C.

(57) ABSTRACT

This invention relates to compositions and methods for eliciting an immune response against a parasite of the genus *Plasmodium* in a mammal.

13 Claims, 12 Drawing Sheets

```
                    a            1 ☆☆☆                                    1                              2           3
vivax       ---DEKVVDEVKYSEEVCNESVDLYLLVDGSGSIGYPNWTTKVIPMLNGIINSLSLSRDTINLYMNLFGNYTTELIRLGSGQSIDKRQ    109
falciparum  RDVQNNIVDEIKYREEVCNDEVDLYLLMDCSGSIRRHNWVNHAVPLAMKIIQQLNLNDNAIHLYVNVFSNNAREIIRLHSDASKNEK        113
cynomolgi   -------EIKYSEEVCNESVDLYLLDSGGSIGYPNWTTRVIPMLSGIIGNLSLSRDAINLYMSLFANHTELIRLGSGPSVDKKL              79
knowlesi    ----DQKIVDEVKYNEEVCNEKVDLYLLVDGSGSIGYANWITRVIPMLTGLIENLNLSKDSINLYMSLFASHTELIRLGSGPSMDKKQ        109
berghei     -------QEILDEIKYSEEVCNEQIDLHLILDSGSSIGHSNWISHVIPMLTTLVDNLNISRDEINISMTLFSTYARELVRLKRYGSTSKAS     108
yoelii      -------QEILDEIKYSEEVCTEQIDIHILILDSGSSIGYSNWKAHVIPMLNTLVDNLINISNDEINVSLTLFSTNSRELIKLKGYGSTSKDS    108
gallinaceum ----ADQIVDEITYNEQICEHEKVDLYLLMDGSGSIGYDNWIISYAVPLVEEIVQNLNISKQGIHLYLSVFTHILKEYIPLNSIFSTNRDF     109
relictum    ---------------HEKVDLYIIMDGSGSIGYDNWIISYAVPLVYDIVKNLNVSNDGIHHLYLSVFTHYLREYIKLGSSLSTNREF          58

3                              4        ☆                           4                      5
vivax       ALSKVTELRKTYTPYGTTNMTAALDEVQK-ILNDRVNREKAIQIVILMTGVPNSKYRALEVANKLKQRNVSLAVIGIGQGINHQFNR         196
falciparum  ALSIIKSLLSTNLPYGRTNLFTDALLQVRK-HLNDRINRENANQLIVIILTDGIPDSIQDSLKESRKLINDRGVKIAVFGIGQGINVAFNR     200
cynomolgi   ALDSSSELRKTVPYGATNMSSALAEVEM--HLKDRVNREKAIQLVILILTDGVPNNKFRVELSKALKERNVKLAVIGIGHGINHHFNR        166
knowlesi    ALNVVRDLRKGYEPYGNTSMSSALSEVEM-HLKDRVNRPNAIQLVIIMTDGIPNNKYRALLLSRALKERNVKLAVIGIGQGINHQYNK        196
berghei     LRFITAQLQNNYSPHGTNLTSALLNVDN--LIQKKMNRPNAIQIVIILTDGIPNNLKKSTTVVNQLKKKDVNVAIIGVGAGVNNMFNR        195
yoelii      LRFTLAFLQNNYSPNGNTNLTSALLVVDT-LINERMYRPDAIQLAIILTDGIPNDLPRSTAVVHQLKRKHVNVAIIGVGAGVNNEYNR        195
gallinaceum ALNVIRSLRTKYSQNGSTNLFTLALSRVIKNYFLTKGSREDAVQLVIIFTDGSPDNKESAMKEVNKLKKMKAKFAVIGVGMGINKEFNK       197
relictum    ALNIIENLKNKYYLHGSTNLTIALSRVLQDNFIKKKGREDAVQLILIFTDGAPDDKETAMQEVVLKKMNAKFSVIGVGMGINREFNK         146

| | | |
|---|---|---|
| vivax | LIAGCRPREPNCKFYSYADWNEAVALIKPFIAKVCTEVERVANCGPWDPWTACSVTCGRGTHSRSRPSLHEKCTHMVSECEEGECP | 283 |
| falciparum | FLVGCHPSDGKCNLYADSAWENVKNVIGPFMKAVCVEVEKTASCGVWDEMSPCSVTCGKGTRSRKREILHEGCTSEIQEQCEEERCP | 287 |
| cynomolgi | LIAGCSPRQENCKFYSYAEWNEAVALIKPFIAKVCTEVEKVANCGPWNPWTPCSVTCGKGTHSRSRPLVHEGCTTHMVNECEEQECP | 253 |
| Knowlesi | LMAGCRPRERSCKFYSSADWSEAISLIKPFIAKVCTEVERIAKCGPWDDWTPCSVTCGKGTHSRSRPLLHAGCTTHMVKECEMDECP | 283 |
| berghei | ILVGCG-KLGPCPYYSYGSWDQAQTMIKPFLSKVCQEVEKVALCGKWEEMSECSTTCDNGTKIRKRKVLHPNCAGEMTAPCKVRDCP | 281 |
| yoelii | ILVGCD-RYAPCPYYSSGSWNEAQNMIKPFLTKVCQEVERIAHCGKWEEMSECSTTCDEGRKIRRQILHPGCVSEMTTPCKVRDCP | 281 |
| gallinaceum | SLVGCPLKEKKCDLYSEASWNEVQNVIAPFLKEVCIEVEKVAHCGSWGEMSPCSVTCGEGVRTRREVLHKGCTDHMTVLCEKPNCP | 284 |
| relictum | RLVGDCSPYEEKCDLYSEASWVDVKDIIAPFLKKVCVEIEKVAHCGSWGEWTPCSVTCGEGIKTRKRNILHKGCSDHMNALCEKPECP | 233 |

FIG. 2B (Cont.)

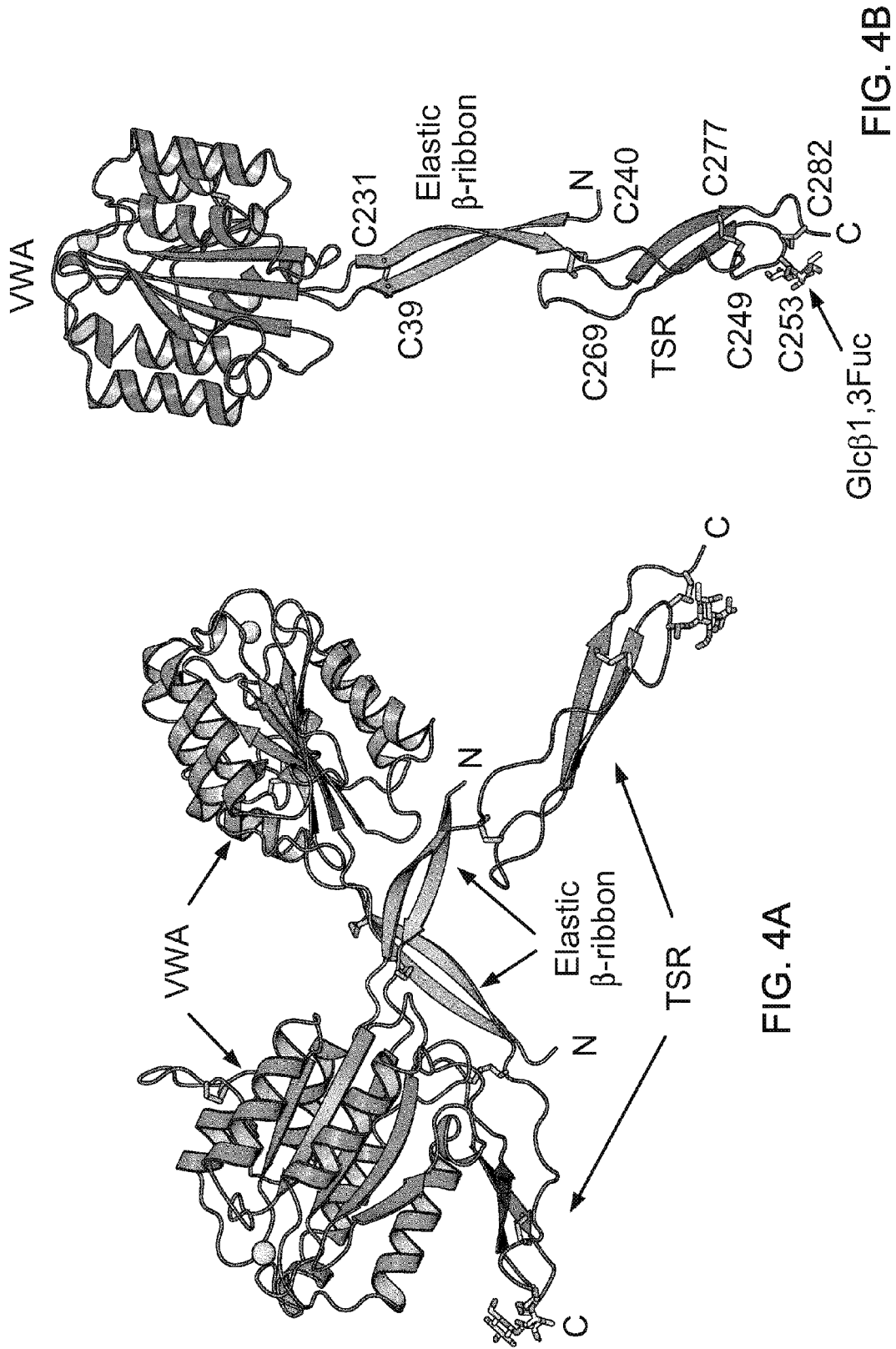

```
falciparum 3D7      1  MNHLGNVKYIVIVFLIFFDLFIVNGRDVQNNIVDEIKYREEVCNDEVDLYLIMDCSGSIRRHNMVNHAVPLAMKLIQQLN    80
          vivax     1  MKLLQNKSYLLVVFLYVSIFARG----DEKVVDEVKYSEEVCNESVDLYLIMDGSGSIGYPNWITKVTPMINGLINSLS    76
knowlesi strain H   1  MKLLQNKSYLLVVFLYVSIFARG----DQKIVDEVKYNEEVCNEEVDLYLIMDGSGSIGYANMITRVIPMLIGLIENLN    76
chabaudi chabaudi   1  MKLLGNSKYLFVLL-CISVFLSG----QEIPDVIKINEEVCNEKIDVHILMDGSGSIGQSNMITYLIPTLTLVENLN    75
         cynomolgi  1  ----------------------------EIKYSEEVCNESVDLYLLLDGSGSIGYPNMLTRVIPMLSGLLGNLS      46
      yoelii yoelii 1  MKLLGNSKYIFVVLL-CISVFLNG----QETLDEIKYSEEVCTEQIDIHILLDGSGSIGYSNMKAHVIPMINTLVDNLN   75
           berghei  1  MKLLGNSKYFFVVLL-CISVFLNG----QEILDEIKYSEEVCNEQIDLHILLDGSGSIGHSNMLSHVIPMLFTLVDNLN   75
        gallinaceum 1  MKIFFLSNKFLLFIFF-YFSTVVKGA---DQIVDEITYNEQICHEKVDLYLIMDGSGSIGYYNMVTYAVPLVEEIVQNLN  76
          relictum  1  -------------------------------HEKVDLYIIMDGSGSIGYDNMLSYAVPLVYDIVKNLN            37 falciparum 3D7     81  LNDNAIHIYASVFSNNAREIIRLHSDASKNKEKALIIIKSLLSTNLPYGKTNLTDALLQV-RKHLNDRINRENANQLVVI 159
          vivax    77  LSRDTTNLYMNLFQNYTTELIRIGSGQSIDKRQALSKVTELRKTYTPYGTTNMTAALDEV-QKHLNDRVNREKAIQLVIL 155
knowlesi strain H  77  LSKDSTNLYMSLFASHTTELIRIGSGPSMDKKQALNVRDIRKGYEPYGNTSMSSALSEV-EMHLKDRVNRPNAIQLVIL  155
chabaudi chabaudi  76  ISKSAINVIMILFSTYZNKLIIPKGYGSTSINELLFVIEYIKIKYSPHGGINLIDALVNV-ANLIQNKLVRPDAIQLVIV 154
         cynomolgi 47  LSRAINIYMSLFANHTTELIRIGSGPSVDKKIALDSSSELRKTYVPYGATNMSSAIAEV-EMHLKDRVNREKAIQLVIL  125
      yoelii yoelii 76  ISNDEINVSLTLFSTNSRELIKLKGYGSTSKDSIRFILAHLQNNYSPNGNTNLTSALLVV-DTLINERMYRPDAIQLAII 154
           berghei  77  ISRDEINISMTLFSTYAREIVRIKRYGSTSKASIRFIIAQLQNNYSPHGTTNLTSAILNV-DNLIQKKMNRPNAIQLVII 154
        gallinaceum 77  ISKQGTIHLYLSVFTHI-KEYIPINSIFSTNRDFALNVTRSLRTKYSQNGSTNLTIALSRVLKNYFLTKGSREDAVQLVII 156
          relictum  38  VSNDGIIHLYLSVFTHY-REYIKIGSSLSTNREFALNIIENLKNKYYLHGSTNLTIALSRVLQDNFIKKKGREDAVQLILI 117 falciparum 3D7    160  LTDGLPDSIQDSLKESRKLSDRGVKTAVFGLGQGINVAFNRFLVG---------CHPSDGKCNLYADSAWENVKNVIGPFMKA  233
          vivax   156  MTDGVPENSKYRALEVANKLKQRNVSLAVIGVGQGINHQFNRLIAG--------CRPRERSCKFYSADWSEAISLIKPFIAK    229
knowlesi strain H 156  MTDGIPENNKYRALELSRALKERNVKLAVIGIGQGINHQYNKIMAG--------CRPRERSCKFYSSADMSEAISLIKPFIAK    229
chabaudi chabaudi 155  LTDGLPNSLKKAAETVDALKRINVKVALIGVGPDINHKYNRLLVG--------CA-RLGRCPYYASGSWDKAQAMIKPFLTK    227
         cynomolgi 126  LTDGVPENNKFRVVELSKALKEKNVKLAVIGHGHGINHHFNRLIAG--------CSPRQENCKFYSAFWNEAVALIKPFIAK    199
      yoelii yoelii 155  LTDGLPNDLPRSTAVVHQLKRKHVNVALIGVGAGVNNEYNRLLVG--------CD-RYAPCPYYSSGSWNEAQMIKPFLTK    227
           berghei  155  LTDGIPNNLKKSTTVVNQLKKDVNVAIIGVGAGVNNMFNRIIVG---------CG-KLGPCPYYSYGSWDQATMIKPFLSK    227
        gallinaceum 157  FTDGSPDNKESAMKEVNKLKKMKAKFAVLGVGMGINKEFNKSLVG--------CPLKEKKCDLYSEASWNEVQNVIAPFLKE    230
          relictum  118  FTDGAPDDKFTAMQFVVKT-KKMNAKFSVTGVGMGTNRFFNKRTVD--------CSPYFFKCDLYSFASMTVKDTTAPFIKK    191
```

FIG. 5A

| | | | |
|---|---|---|---|
| falciparum 3D7 | 234 | VCVEVEKTASCGVMDEWSPCSVTCGKGTRSRKREILHEGCTSELQEQCEEERCLPKR------------------------- | 290 |
| vivax | 230 | VCTEVERVANCGPWDPWTACSVTCGRGTHSRSRPSLHEKCTTHMVSECEEGECPVEP------------------------- | 286 |
| knowlesi strain H | 230 | VCTEVERIAKCGPWDDWTPCSVTCGKGTHSRSRPLLHAGCTTHMVAECEMDECPVEP------------------------- | 286 |
| chabaudi chabaudi | 228 | VCQEVERIAQCGQMGEWAECTTICGNGTRTRSRIVLHPGCIGQMTGPCNVRDCPPEPVAPPVA----------------- | 290 |
| cynomolgi | 200 | VCTEVEKVANCGPWNPWTPCSVTCGKGTHSRSRPLVHEGCTTHMVNECEEQECPVEP-------------------------- | 256 |
| yoelii yoelii | 228 | VCQEVERIAHCGKWEEWSECSTTCDEGRKIRRQILHPGCVSEMTTPCKVRDCPQIPI-PPVIPNKIPEKPSNPEEPVNP | 306 |
| berghei | 228 | VCQEVEKVALCGKWEEWSECSTTCDNGTKIRKRKVLHPNCAGEMTAPCKVRDCPPKPVAPPVIPIKVPDVPVKPVEPI- | 305 |
| gallinaceum | 231 | VCIEVEKVAHCGSMGEWSPCSVTCGEGVRTRRREVLHKGCTDHMTVLCEKPNCPEIV---------------------- | 287 |
| relictum | 192 | VCVEIEKVAHCGSMGEWTPCSVTCGEGIKTRKRNILHKGCSDHMNALCEKPECPAII---------------------- | 248 |

| | | | |
|---|---|---|---|
| falciparum 3D7 | | ---------------------------------------------------------------- | |
| vivax | | ---------------------------------------------------------------- | |
| knowlesi strain H | | ---------------------------------------------------------------- | |
| chabaudi chabaudi | | ---------------------------------------------------------------- | |
| cynomolgi | | ---------------------------------------------------------------- | |
| yoelii yoelii | 307 | NDPNDPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPNNPSN | 386 |
| berghei | | ---------------------------------------------------------------- | |
| gallinaceum | | ---------------------------------------------------------------- | |
| relictum | | ---------------------------------------------------------------- | |

| | | | |
|---|---|---|---|
| falciparum 3D7 | | ---------------------------------------------------------------- | |
| vivax | | ---------------------------------------------------------------- | |
| knowlesi strain H | | ---------------------------------------------------------------- | |
| chabaudi chabaudi | | ---------------------------------------------------------------- | |
| cynomolgi | | ---------------------------------------------------------------- | |
| yoelii yoelii | 387 | PNNPNPKKRNPKRRNPNKPKPNKPKPNKPNEPSNPKPNEPSNPNKPNPNEPSNPNKPNPNEPSNPNKPNPNEPLN | 466 |
| berghei | | ---------------------------------------------------------------- | |
| gallinaceum | | ---------------------------------------------------------------- | |
| relictum | | ---------------------------------------------------------------- | |

FIG. 5B

```
falciparum 3D7   291 ----------------------------------EPLDVP------DEPED--------DQ------PRPRGDNFA------VEKPNENIID---NN 324 vivax   287 ----------------------------------EPLPVPAPL-PTVPED--------VN------PRDTDDE-N------EN-PNFNKGL--DV 322
knowlesi strain H 287 ---------------------------------EPVPVPAPV-PPTPED--------EN------PRTTDEE-D------DH-PNFHQGL--DV 322
chabaudi chabaudi 291 ---------------------------------PLIIP------EM--------------------PI--------------------------- 299
     cynomolgi   257 ----------------------------------EPVPVPAPF-PTVPED--------LK------PRNTDDD-D------DDHPNFHKEL--DV 293
   yoelii yoelii 467 PNEPSNPNEPSNPNAPSNPNEPSNPNEPSNPNEPSN-------------------PNEPSN--PNEPSNPKKPSNPNEPSNPNEPL-----N 532
        berghei 306 ----------------------------------EPAE------------------PAEPAE--P------------------AEPAEPA---E 324
     gallinaceum 288 ---------------------------------KPNITD--V-PDVPDE---------E------PEPIPEEKK------PEPVPEEKKP---ESA 323
       relictum 249 ---------------------------------KPSVTD---I-PKVIPE--------------DNRRGDVPDNVPENKKRGDVPDYFPEDNKPLVPDNV 297 falciparum 3D7   325 PQEPSP--NPEEGKGEN-PNGFD-------LDENPENPNPNPNP-PNPNPNP---DIPEQEPNI---PE------DSEKE 386 vivax   323 PDEDDDEVPPAN-EGAD-GNPVE-------ENVFPPADDSVPDESNVLPLPPAVPGGSSEEFPADVQN---------------- 381
knowlesi strain H 323 PDVEND-VPPEN-DGGD-GNPFE-------ENFFPPGDDTVPDESNVIPVPPTVPGGSNSEFSSDVENAAQYPE--NPENP 391
chabaudi chabaudi 300 -APVEPEEPNEPEELGEPEKLIDPKEPIIPEE--PIIP---EEPIIPEEPIIPEEPIIPEEP-IIPEEP 373
     cynomolgi   294 PDVEDD-VPPEN-D-VD-GNPAE-------ESDFPPTDDAVPEESNVLPVPPVVPGGSTDEFPTDVRNS--PM------NPENP 358
   yoelii yoelii 533 PNEPSNPNEPSN----PNEPSNPE----EPSNPKEPSNPNEPSNP-EEP-NPEEPSNPKEPSNPEEPIN-PEEL--NPKEP 600
        berghei 325 PAEPAEPAEPAE---PAEPAEPA----EPAEPAEPAEPAEPAEP-AEPAKPAEPAEPAEPAEPAEPAEPVN-PD--NPILP 391
     gallinaceum 324 PEEKNPESVPEEKK--PESVP-----EEKEPE--SVPEEKEP-E---SVPEEKEPE---SAPEEKK-PE--SDPEEK 381
       relictum 298 PNN-DPDNAPENKKRGDVPDYFP-------ENNQPEVPDNAPEDNQP-EVPDNVPEENQPEVPYNVPEENQ-PEVPDNVPEEN 370 falciparum 3D7   387 VPSDVPKN----------------------PEDDREENF--DIPKKPE-----------------NKHDNQ---------NNLPN 421 vivax   382 ------------ENPENSEN-----------------------NPDSPEELPMEQE--------------VPQDNN------VNEPE 405
knowlesi strain H 392 ----------------------PENPENQNNPEDFPMEPD---------MSADNK--------INEPT 428
chabaudi chabaudi 374 IIPEEPIIQE------EPEIPVEPLNPGEIENPDIIPEKPIEQIIVPDVEPKLPIIPEKNTE-----IPNNLPE 436
     cynomolgi   359 ENSEYPEN----------------PESPENPNNPEESPMEQE--------------VPQDNN-------INEPE 395
   yoelii yoelii 601 SNPEESNPKEPINPEESNPKEPINPEDNENPLIIQDEPIEPRNDSNVIPILPIIPQKGNN----IPSNLPE 667
        berghei 392 IKPEE-----PSGGAEPINPEV-ENPFIIPDEPIEP------------------------- 421
     gallinaceum 382 KLEPIPEGKK-IEPIPEEEKLEPIPEEKKPESVTEDRESEPVPDGEAENVPQNIPDDEQEEKISGDIPNDEELIPKNEPD 460
       relictum 371 QPE-VPDN--------VPEDRNPE-IPEEKKPENIPENRKEEII----EYIPKNIPDDV------EIIPNENPR 424
```

FIG. 5C

```
falciparum 3D7      422 --DKSDRYIPYSPLSPKVLDNERKQSDPQSQDNNGNRHVP--N------SEDRETRPHGRNNENR--SYNRKHNNTPKHPE 490
          vivax     406 RSDSNGYGVNEKVIP-NPLDNERDVANKNKTVHPGRK-------D---SARDRYARPHGSTHVN--NNRANENSDIPNNPV 473
knowlesi strain H   429 NPSDSGQGIPENVIP-TPINNEKDIINKNKAVYPNGS-------N---QSHDRYPKPHRNAGGY--DNNPNANSDIPEGPF 496
chabaudi chabaudi   437 KPDGSQVEYPK---PNGDGDNPNNGTNSNKNIPNQNV-TPGDNDPSRNQFERIPKPHQSNDEYVYDDYIKNNEPSEPETQ 512
       cynomolgi    396 RSDGKVNGINHKLIP-KPMDNEKDI-NKNKKVHPSSS------N----HAHDRYARPHRSSGGN--DNGRIANSDLPRAPV 462
   yoelii yoelii    668 NPSDSEVEYPR---PNDNGENSNNTMKSKKNIPNEPIPSPGDN-PYKGHEERIPKPHRSNDDYVYDNNVNKNNKDEPEI- 742
         berghei
     gallinaceum    461 DIKRNEYDITPNIIPPKDTYNDNEITNPISE-ED-NE-------N---KTKVEDRVPRPHNTDSEY--IPPKRDNHKDEPSRR 529
        relictum    425 IIIKDQRHLPPQVVPAKNIHNENQIINKVPE-HNGNI------N---KTTVEDRELRPHNTDNEY--IRPRRNDYKVEPSTE 494 falciparum 3D7      491 REEHEKPDNNKKKAG-SDNKYKIAGGIAGGLALLACAGLAYKFVVPGAATPYAG-EPAPFDETLGEEDKDLDEPEQFRLP 568
          vivax     474 PSDYEQPEDKAKKS--SNNGYKIAGGVIAGLALVGCVGFAYNFVAGGGAAGMAG-EPAPFDEAMAEDEKDVAEADQFKLP 550
knowlesi strain H   497 SSEEEQPEDKGKKS--SNNGYKIAGGVIAGLALVGCVGFAYNFVSSGGAAGMAG-EPAPFDEAMAEDEKDAGEADQFKLP 573
chabaudi chabaudi   513 NPNENENNKNKGKPKSNNGYKIAGGIIGGLAIIGCAGVAYNFIASSGAAGLVG-EPTPFEDVMPDDKENGENEQFKLP 591
       cynomolgi    463 ASDYEQPEDKGKKS--SNNGYKIAGGVIAGLALVGCVGFAYLFVASGGAAGMAG-EPAPFDEAMAEDKDTAEADQFKLP 539
   yoelii yoelii    743 -PNNEYEEDKNKNQSKSNNGYKIAGGIIGGLAIIGCAGVGYNFIAGSSAAGLAGAEPAPFEDVIPDDDKIVENEQFKLP 821
         berghei
     gallinaceum    530 KRENEGTQGKTKKTSLNDNKYKIAGGIIGGLALLGCAGFAYKFLTQTPTPITS-EAAPFDDVLAEGEKDIEENEQFKLP 608
        relictum    495 NVENENSEEKNKKAP-SDNKYKIAGGIIGGLALLGCAGFAYKFLAHAPTPMTS-EGAPFNDVLGEGEKDIEENEQFK-- 570 falciparum 3D7      569 EENEWN------ 574
          vivax     551 EDNDWN------ 556
knowlesi strain H   574 EDNDWN------ 579
chabaudi chabaudi   592 EDNDWNEMBCAACAHAACAAF 612
       cynomolgi    540 EDNDWN------ 545
   yoelii yoelii    822 EDNDWN------ 827
         berghei
     gallinaceum    609 EDNDWN------ 614
        relictum
```

FIG. 5D

DEKVVDEVKYSEEVCNEQVDLYLLVDGSGSIGY
PNWITKVIPMLNGLINSLSLSRDTINLYMNLFG
SYTTELIRLGSGQSIDKRQALSKVTELRKTYTP
YGTTSMTAALDEVQKHLNDRVNREKAIQLVILM
TDGVPNSKYRALEVANKLKQRNVRLAVIGIGQG
INHQFNRLIAGCRPREPNCKFYSYADWNEAVAL
IKPFIAKVCTEVERVANCGPWDPWTACSVTCGR
GTHSRSRPSLHEKCTTHMVSECEEGECP
SEQ ID NO:16

FIG. 6A

RDVQNNIVDEIKYREEVCNDEVDLYLLMDGSGSIRRH
NWVNHAVPLAMKLIQQLNLNDNAIHLYASVFSNNAR
EIIRLHSDASKNKEKALIIIKSLLSTNLPYGKTSLTDALLQVRK
HLNDRINRENANQLVVILTDGIPDSIQDSLKESRKLSDRGV
KIAVFGIGQGINVAFNRFLVGCHPSDGKCNLYADSAWEN
VKNVIGPFMKAVCVEVEKTASCGVWDEWSPCSVTCGKG
TRSRKREILHEGCTSELQEQCEEERCLPKREPLDVPDEP
SEQ ID NO:17

FIG. 6B

CONFORMATION-STABILIZED TRAP ANTIGENS

CLAIM OF PRIORITY

This application is a U.S. National Phase Application under 35 U.S.C. §371 of International Patent Application No. PCT/US2013/026461, filed on Feb. 15, 2013, which claims the benefit of U.S. Provisional Application Ser. Nos. 61/600,567 and Ser. No. 61/600,570, both filed on Feb. 17, 2012. The entire contents of the foregoing are incorporated herein by reference.

FEDERALLY SPONSORED RESEARCH OR DEVELOPMENT

This invention was made with Government support under Grant No. AI095686 awarded by the National Institutes of Health. The Government has certain rights in the invention.

TECHNICAL FIELD

This invention relates to compositions and methods for eliciting an immune response against a parasite of the genus *Plasmodium* in a mammal.

BACKGROUND

Malaria is caused by a eukaryotic protist parasite of the genus *Plasmodium*. Transmission is typically by the bite of infected female *Anopheles* mosquitoes, which carry *Plasmodium* sporozoites in their salivary glands, though congenital transmission and transmission by blood transfusion is also possible. Within minutes after infection of a mammalian host, the sporozoites enter the blood stream and migrate to the liver, where they infect hepatocytes, mature and release thousands of merozoites. The parasites then enter the bloodstream, infecting red blood cells.

Malaria is a major health problem to residents and visitors in much of the tropics and subtropics, with 250 million cases of fever and approximately one million deaths annually (2005 WHO World Malaria Report 2008).

SUMMARY

The present invention is based, at least in part, on the discovery of new vaccines (i.e., compositions that elicit an immune response in an animal, e.g., a mammal, e.g., a human) against malaria-causing parasites for use in subjects who may be, or who have been, exposed to such parasites. Thus described herein are antigens, nucleic acids encoding those antigens, host cells and transgenic animals expressing the antigens, and methods of using the antigens as vaccines to elicit an immune response in mammalian subjects.

Thus the invention provides *Plasmodium* TRAP proteins that include one or more mutations described herein.

In a first aspect, the invention provides *Plasmodium falciparum* Thrombospondin-Related Anonymous Protein (TRAP) antigens, wherein the antigen sequence includes one or more of the following (numbering relative to SEQ ID NO:5): Mutation at Cysteine 55 to a non-cysteine amino acid, e.g., Glycine, Serine, or Alanine; Mutation of N-linked glycosylation sites, e.g., mutation of N or (S/T) in the carbohydrate-encoding N-X-(S/T), e.g., N132S, S477N, and/or N483S; Mutation of Ala-216/Asn-222 or Lys-224/Gln-78 to cysteine to create a TRAP that is stabilized in the open conformation; Mutation of Asn-213/Ala-233, Ala-216/ Phe-230, or Met-231/Gln-78 to cysteine to create a TRAP that is stabilized in the closed conformation; Deletion of N-terminal and/or C-terminal residues to create a TRAP fragment that is stabilized in the closed conformation comprising V47-V238; and/or Deletion of N-terminal and/or C-terminal residues to create a TRAP fragment that is stabilized in the open conformation comprising V47-M231.

In some embodiments, the *falciparum* or *vivax* deletion mutants include additional amino acids on one or both ends, e.g., one, 2, 3, 4, 5, 6, 7, 8, 9, 10, 11, 12, 13, 14, 15, 16, 17, 18, 19, 20, 21, 22, 23, 24, 25, 26, 27, 28, 29, or thirty additional amino acids; the deletion mutants can include all of the beta-ribbon as shown in FIGS. 6A-6B.

In some embodiments, the sequence is a mutated *P. falciparum* sequence comprising a sequence that is at least 80% identical to SEQ ID NO:5, e.g., at least 85%, 90%, or 95% identical to SEQ ID NO:5. In some embodiments, the sequence lacks the signal sequence, e.g., lacks amino acids 1-24 of SEQ ID NO:5, e.g., is at least 80% identical to amino acids 25-574 of SEQ ID NO:5, e.g., at least 85%, 90%, or 95% identical to amino acids 25-574 of SEQ ID NO:5.

In another aspect, the invention provides *Plasmodium vivax* Thrombospondin-Related Anonymous Protein (TRAP) antigens wherein the antigen sequence comprises one or more of the following (numbering relative to SEQ ID NO:6): Mutation of N-linked glycosylation sites, e.g., mutation of N or (S/T) in the carbohydrate-encoding N-X-(S/T), e.g., S42Q, N91S, N128S, and/or S180R; Mutation of Ser-212/Glu-218, Val-220/Ser-74 to cysteine to create a TRAP that is stabilized in the open conformation; Mutation of Ser-212/Phe-226, Ile-223/Met-67, Ile-227/Ser-74 to cysteine to create a TRAP that is stabilized in the closed conformation; Deletion of N-terminal and/or C-terminal residues to create a TRAP fragment that is stabilized in the closed conformation comprising amino acids V43-V234; and/or Deletion of N-terminal and/or C-terminal residues to create a TRAP fragment that is stabilized in the open conformation comprising amino acids V43-I227.

In some embodiments, the *falciparum* or *vivax* deletion mutants include additional amino acids on one or both ends, e.g., one, 2, 3, 4, 5, 6, 7, 8, 9, 10, 11, 12, 13, 14, 15, 16, 17, 18, 19, 20, 21, 22, 23, 24, 25, 26, 27, 28, 29, or thirty additional amino acids; the deletion mutants can include all of the beta-ribbon as shown in FIGS. 6A-6B.

In some embodiments, the sequence is a mutated *P. vivax* sequence comprising a sequence that is at least 80% identical to SEQ ID NO:6, e.g., at least 85%, 90%, or 95% identical to SEQ ID NO:6. In some embodiments, the sequence lacks the signal sequence, e.g., lacks amino acids 1-25 of SEQ ID NO:5, e.g., is at least 80% identical to SEQ ID NO:6, e.g., at least 85%, 90%, or 95% identical to amino acids 26-556 of SEQ ID NO:6.

In another aspect, the invention also provides fusion proteins include a first portion consisting essentially of a TRAP antigen protein as described herein, and at least a second portion comprising one or more of an adjuvant, carrier, or protein purification sequence, e.g., a FLAG sequence or a 6His sequence. In some embodiments, the carrier comprises a hepatitis B surface protein.

In another aspect the invention provides nucleic acids encoding an antigen or fusion protein of any of claims; vectors comprising the nucleic acids; and host cells expressing the nucleic acids or vectors.

In a further aspect, the invention provides compositions comprising one or more of the antigens, fusion proteins, or nucleic acids described herein, and pharmaceutical compositions comprising one or more of the antigens, fusion proteins, or nucleic acids described herein, and a physiologically acceptable carrier. In some embodiments, the compositions include an adjuvant.

In yet another aspect, the invention provides methods of inducing an immune response in a mammal The methods include administering to the subject a therapeutically effective amount of one or more of the antigens, fusion proteins, or nucleic acids described herein, e.g., a pharmaceutical composition comprising one or more of the antigens, fusion proteins, or nucleic acids described herein. In some embodiments, the pharmaceutical composition further comprises an adjuvant.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2B shows an alignment of the N-terminal portion of the mature ectodomain (without the signal sequence) of exemplary TRAP sequences, i.e., up to the end of the TSR domain shown in FIG. 1, of sequences from *Plasmodium* species Vivax (SEQ ID NO:17); *falciparum* (SEQ ID NO:18); *cynomolgi* (SEQ ID NO:19); *knowlesi* (SEQ ID NO:20); *berghei* (SEQ ID NO:21); *yoelii* (SEQ ID NO:22); *gallinaceum* (SEQ ID NO:23); and *relictum*(SEQ ID NO:24).

FIG. 4A is a ribbon diagram of two molecules of *P. vivax* TRAP in an asymmetric unit.

FIG. 4B is a ribbon diagram of *P. vivax* TRAP showing three domains: VWA, elastic beta-ribbon and TSR domains. The metal ions are shown as spheres. The O-linked glycans are shown as sticks and labeled.

FIGS. 5A-D show an exemplary alignment of reference Plasmodium TRAP sequences, as follows:

| GenBank Acc No. | Title | SEQ ID NO: |
|---|---|---|
| XP_001350088.1 | Thrombospondin-related anonymous protein, TRAP [*Plasmodium falciparum* 3D7] >gi|160691|gb|AAA29767.1| | 5 |
| XP_001614147.1 | sporozoite surface protein 2 [*Plasmodium vivax* SaI-1] >gi|148803021|gb|EDL44420.1| | 6 |

-continued

| GenBank Acc No. | Title | SEQ ID NO: |
|---|---|---|
| XP_002259987.1 | sporozoite surface protein 2 [*Plasmodium knowlesi* strain H] >gi|193810060|emb|CAQ41254.1| | 7 |
| PCHAS_135440 (plasmodb)) | hypothetical protein [*Plasmodium chabaudi chabaudi*] >gi|56520404|emb|CAH78071.1| | 8 |
| CAA73140.1 | thrombospondin related adhesive protein [*Plasmodium cynomolgi*] | 9 |
| EAA22580.1 | sporozoite surface protein 2 precursor [*Plasmodium yoelii yoelii* 17XNL] >gi|45645179|sp|Q01443.2| | 10 |
| CAH99602.1 | sporozoite surface protein 2 [*Plasmodium berghei* strain ANKA] >gi|56497475|emb|CAH99602.1| | 11 |
| AAC47461.1 | thrombospondin-related anonymous protein [*Plasmodium gallinaceum*] | 12 |
| AAF00021.2 | thrombospondin-related anonymous protein TRAP [*Plasmodium relictum*] | 13 |

In FIGS. 5A-D, the fragments of *falciparum* and *vivax* TRAP that were used in the crystallization assays described herein are underlined. The triangle indicates the nonconserved cysteine (C55) in falciparum. Asterisks above sequences indicate potential N-linked glycosylation sites. The O marks a Thr glycosylation which is present in the *Vivax* structure and is expected to be present in all TRAP structures.

FIGS. 6A and 6B show the N-terminal sequences of *vivax* (6A, SEQ ID NO:16) and *falciparum* (6B, SEQ ID NO:17) TRAP, with the elastic b-ribbon underlined, and the VWA region (which is included within the elastic b-ribbon) double underlined.

FIG. 7 is a set of four ribbon diagrams of two molecules of *P. falciparum* TRAP in the open (left column) and closed (right column) configurations, with the wild type (top row) and conformation-stabilizing disulfide mutations (bottom row).

Figure 8:
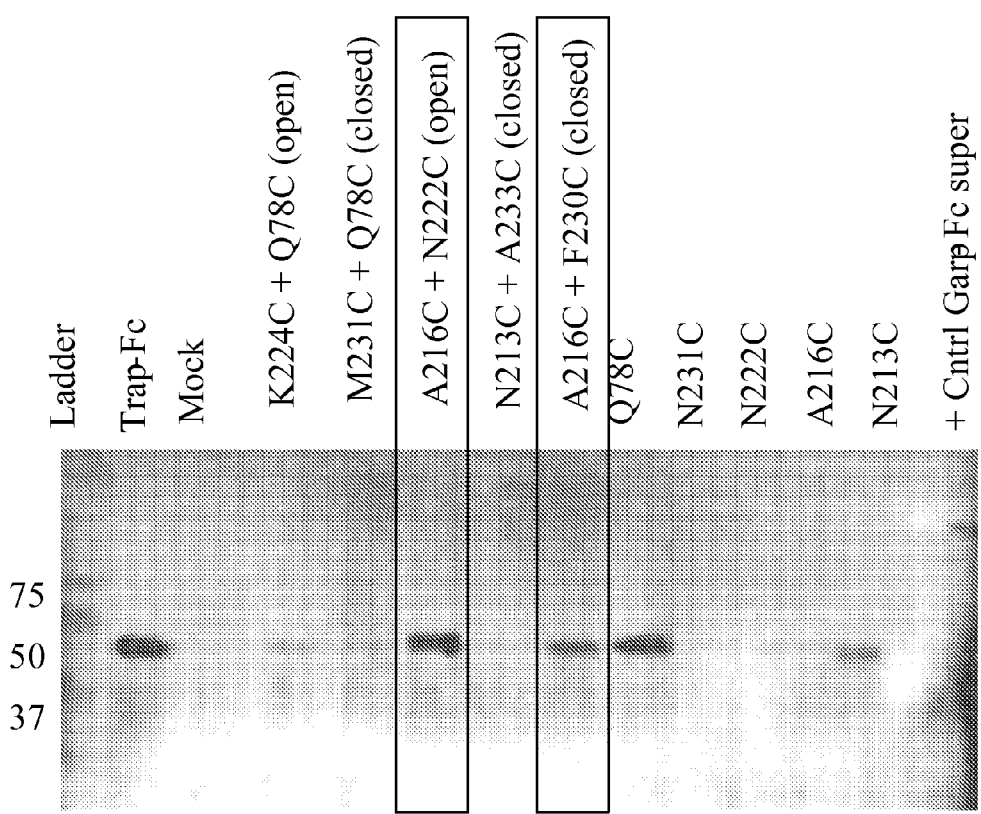

FIG. 8 is an image showing the results of PAGE analysis of the indicated TRAP disulfide mutants.

DETAILED DESCRIPTION

The goal of anti-sporozoite, or pre-erythrocytic vaccines is the development of sterilizing immunity that kills sporozoites (e.g., in mammals, either before infection of the liver, or during development in liver cells), before merozoites are released and begin the erythrocytic stage of the *plasmodium* life cycle (Vekemans and Ballou, 2008). The numbers of sporozoites released by a mosquito bite and the numbers of infected liver cells are very small. Perhaps for this reason, this phase of infection is asymptomatic, sterilizing immunity is never seen to develop in natural infections, and immune responses to pre-erythrocytic antigens are usually weak, if detectable at all. However, the pre-erythrocytic stage is extremely attractive as a vaccine candidate, because usually only one gene is present for each protein (albeit with variation between strains). In contrast, the erythrocytic stage often has cassettes with 50 or more variant proteins for each important antigenic target, so once immunity develops to one, parasites with expression of a different gene in the cassette can be selected.

Animal studies have emphasized the importance of T cells in pre-erythrocytic immunity. Lysis of infected liver cells before merozoites can mature and be released appears to be the key step; however, antibodies also contribute to pre-erythrocytic immunity (Overstreet et al., 2008; Schofield et al., 1987).

Thrombospondin-related Anonymous Protein (TRAP)

Figure 1:
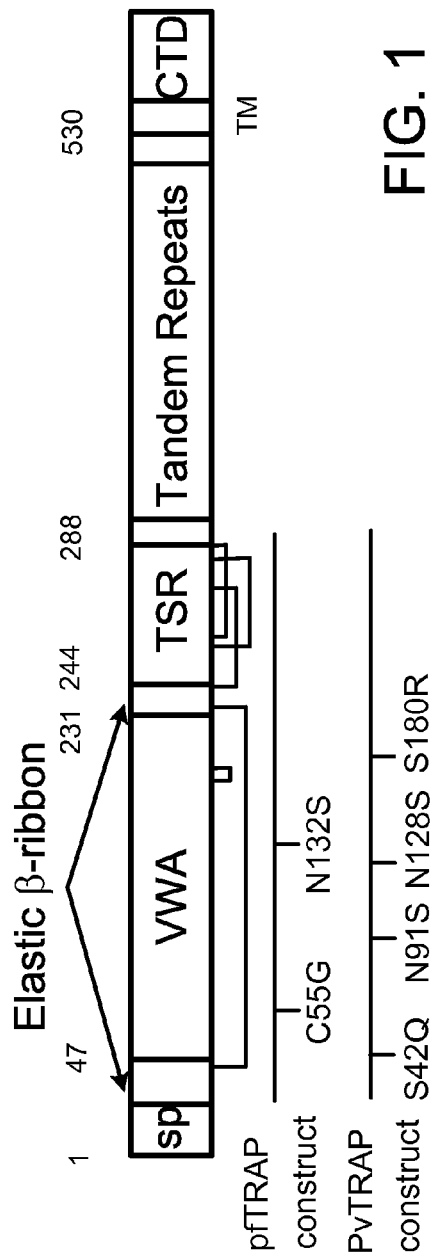
FIG. 1 is a schematic illustration of the structure of TRAP.

TRAP (also known as sporozoite surface protein 2 or SSP2) is one of the major surface components of sporozoites, the form of malaria parasite that mosquitoes transfer to humans. Intracellular TRAP localizes to the micronemes, a set of organelles that secrete their contents to the apical surface of the parasite during cell invasion. TRAP is also found in a patchy distribution on the plasma membrane of sporozoites, where it is translocated to the posterior surface of the parasite during host cell penetration (Kappe et al.). TRAP is responsible for binding to the extracellular environment, and by also connecting to the parasite cytoskeleton, mediates parasite gliding motility and host cell invasion (Sultan et al., 1997). TRAP is required for movement of parasites through host tissues, through cells, and in forming the moving junction required for the formation of the parasitophorous vacuole as the malaria parasite invades the liver cell it infects. TRAP is a transmembrane protein with two extracellular folded domains, a von Willebrand factor A (VWA) or integrin I domain and a TSR domain (FIG. 1). Conformational changes in VWA domains, including in integrin alphaI and betaI domains, and in complement components, regulate their affinity for ligand (Luo et al., 2007; Springer, 2006).

TRAP also has a predicted metal ion dependent adhesion site (MIDAS), which as shown herein indeed binds a metal in the structure. Mutation of MIDAS residues greatly decreases infection, showing the importance of the MIDAS. In integrin I domains, ligand binding occurs to a metal held in the MIDAS. The cytoplasmic tail domain (CTD) of TRAP connects to the actin cytoskeleton through aldolase, permitting functional cooperation between the extracellular adhesive domains and the intracellular actin/myosin motor during gliding and invasion (Buscaglia et al., 2003; Jewett and Sibley, 2003; Kappe et al., 1999).

As described herein, the structure of TRAP has been determined in two different conformational states, termed closed and open. The open conformation binds a metal at its MIDAS. It is likely that the closed conformation binds a metal ion also, although in the particular crystal lattices studied here no metal is bound. It is likely that the open conformation would bind to host receptors that enable sporozoite migration and invasion. However, the open conformation might exist only transiently on the sporozoite surface, and the closed conformation is likely to predominate in the absence of binding to a host ligand. Thus, described herein are antigens that allow the production of antibodies to either conformation, and the antigens can be used singly or in combination to evoke neutralizing, protective antibodies.

Immunity to parasite proteins in general, and also to TRAP, is important both at the antibody and cellular level. Antibodies can neutralize sporozoites before they reach their target cells in the liver. After infection of liver cells, T lymphocytes can kill liver cells before they burst and release many thousands of parasites that start the next step of infection of red blood cells, for which TRAP is irrelevant. The designed protein and DNA/RNA TRAP vaccines disclosed here can be useful in both types of immunity. Conformation is less important for cellular (T cell) immunity, but knowing the portion of the protein that constitutes the folding unit is important, because expression of this unit in vivo greatly boosts net synthesis by stabilizing the protein and preventing degradation, including degradation by the quality control apparatus in the endoplasmic reticulum. Thus by increasing the amount of protein that is made in vivo, much TRAP protein is available for association with major histocompatibility type I and II molecules for stimulation of cellular immunity.

Disclosed herein are malaria vaccines to thrombospondin-related anonymous protein (TRAP), and methods for making and using them. The species of *Plasmodium* may be the most clinically relevant species, i.e., *falciparum* or *vivax* (for which specific examples are given herein), or other species such as *malariae* or *ovale*, for which sequence alignments may be used to guide construct design (see, e.g., FIG. 2B and FIG. 5). As polymorphisms exist among different *vivax* and *falciparum* strains, variants with these polymorphisms can also be made; see, e.g., Robson et al., Am J Trop Med Hyg 58, 81-89 (1998); Robson et al., Proc Biol Sci 242, 205-216 (1990).

TRAP Vaccines

Described herein are genetically engineered TRAP antigens that are useful in eliciting an immune response in an immunized animal. The TRAP proteins described herein may be optimized in a number of ways, including by mutation and truncation, to enhance expression, conformational homogeneity, and/or antigenicity. As shown herein, immunization with TRAP proteins lacking N-linked glycans and encoding the VWA, elastic ribbon, and TSR domains, or the entire extracellular domain, elicits high-titer antibodies in mice and rabbits. Titers extend at least to dilutions of 125,000 in rabbits and 25,000 in mice. This contrasts with previous studies using TRAP peptides that had shown poor titers and did not provide protection against infection (Gantt et al. Infect Immun 68, 3667-3673 (2000)).

Optimized TRAP Protein Antigens

The TRAP protein antigens described herein can include optimized versions of the TRAP proteins from any of the known *Plasmodium* species, e.g., *vivax; falciparum; chabaudi; cynomolgi; knowlesi; berghei; yoelii; gallinaceum; reichenowi*; and *relictum*. For use in humans, the antigens can be based on *P. vivax, P. falciparum*, or *P. knowlesi. P. knowlesi*-based antigens are useful in immunizing monkeys. A vaccine composition can include more than one, e.g., a combination of antigens based on *P. vivax* and *P. falciparum*. Since polymorphic forms of these proteins exist, a vaccine composition can also include combinations of antigens based on more than one polymorphic form of *P. vivax* or *P. falciparum*. Reference sequences for *falciparum* TRAP proteins include GenBank Acc. No. XP_001350088.1 (*falciparum* 3D7); other sequences can also be used, including GenBank Acc. Nos. XP_001350088.1; AAA29775.1; AAA29771.1; AAQ11895.1; AAQ11894.1; AAQ11892.1; AAA29774.1; AAG12328.1; BAA31173.1; AAA29776.1; BAA31174.1; BAA31188.1; AAA29770.1; AAA29777.1; BAA31181.1; BAA31193.1; BAA31171.1; BAA31187.1; BAA31189.1; BAA31186.1; BAA31170.1; BAA31190.1; BAA31172.1; BAA31191.1; BAA31192.1; AAQ11891.1; BAA31167.1; BAA31177.1; AAA29772.1; BAA31169.1; BAA31180.1; CAA63617.1; P16893.1; BAA31178.1; 1411304A; 1708291A; BAA31182.1; BAA31183.1; AAA29778.1; AAW78134.1; BAA31168.1; AAW78143.1; BAA31194.1; BAA31176.1; BAA31175.1; AAW78169.1; AAA29773.1; AAW78167.1; AAW78171.1; AAC18657.1; AAW78131.1; AAW78160.1; AAW78142.1; AAW78139.1; AAW78172.1; AAW78164.1; AAW78159.1; AAW78155.1; AAW78132.1; AAW78133.1; AAW78130.1; AAW78148.1; AAW78168.1; AAW78144.1; AAW78170.1; AAW78149.1; AAW78165.1; AAW78146.1; AAW78147.1; AAW78151.1; AAW78137.1; AAW78152.1; AAW78138.1; AAW78140.1; AAW78175.1; AAW78135.1; AAW78153.1; AAW78162.1; AAW78141.1; AAW78166.1; AAW78161.1; AAW78163.1;

AAW78158.1; AAW78136.1; AAW78157.1; BAA31195.1; AAW78176.1; AAW78150.1; AAW72737.1; CAE46494.1; CAE46496.1; CAE46497.1; CAE46493.1; CAE46626.1; CAE46492.1; CAE46498.1; and CAE46495.1, as well as sequences having at least 80% identity to any of these sequences, e.g., at least 85%, 90%, or 95% identity. See, e.g., Robson et al., Am J Trop Med Hyg 58, 81-89 (1998); Robson et al., Proc Biol Sci 242, 205-216 (1990).

Reference sequences for *vivax* TRAP proteins include GenBank Acc. No. XP_001614147.1 (*vivax* SaI-1); other sequences can also be used, including GenBank Acc. Nos. AAC97485.1; AAC97484.1; AAK57632.1; AAK57600.1; AAK57621.1; AAK57620.1; AAK57634.1; AAK57628.1; AAK57630.1; AAK57623.1; AAK57637.1; AAK57639.1; AAK57629.1; AAK57636.1; AAK57631.1; AAK57624.1; AAK57612.1; AAK57608.1; AAK57619.1; AAK57595.1; AAK57610.1; AAK57601.1; AAK57599.1; AAK57611.1; AAK57607.1; AAK57598.1; AAK57618.1; AAK57617.1; AAK57597.1; AAK57592.1; AAK57603.1; AAK57638.1; AAK57585.1; AAK57590.1; AEC32940.1; AEC32935.1; AEC32934.1; AAC47463.1; AAK57593.1; AAK57580.1; AAK57578.1; AAK57588.1; AAK57570.1; AAK57567.1; AAK57573.1; and AAK57591.1; as well as sequences having at least 80% identity to any of these sequences, e.g., at least 85%, 90%, or 95%. see, e.g., Robson et al., Am J Trop Med Hyg 58, 81-89 (1998); Robson et al., Proc Biol Sci 242, 205-216 (1990).

Reference sequences for *knowlesi* TRAP proteins include GenBank Acc. No. XP_002259987.1 (*knowlesi* strain H); other sequences can also be used, including GenBank Acc. Nos. XP_002261881.1; XP_002261881.1; CAQ41254.1; CAQ39045.1; AAG24613.1 and AAC47462.1; as well as sequences having at least 80% identity to any of these sequences, e.g., at least 85%, 90%, or 95% identity to any of these sequences.

Reference sequences for chabaudi TRAP proteins include PlasmoDB Acc. No. PCHAS_135440 (*Plasmodium chabaudi chabaudi*); other sequences can also be used, including GenBank Acc. Nos. XP_741796.1, XP_744771.1 and sequences having at least 80% identity to any of these sequences, e.g., at least 85%, 90%, or 95% identity.

Reference sequences for cynomolgi TRAP proteins include GenBank Acc. No. CAA73140.1 (*Plasmodium cynomolgi*); other sequences can also be used, including sequences having at least 80% identity to that sequence, e.g., at least 85%, 90%, or 95% identity.

Reference sequences for *yoelii* TRAP proteins include GenBank Acc. No. EAA22580.1 (*Plasmodium yoelii yoelii* str. 17XNL); other sequences can also be used, including AAA29768.1, XP_731015.1 and sequences having at least 80% identity to any of these sequences, e.g., at least 85%, 90%, or 95% identity.

Reference sequences for *berghei* TRAP proteins include GenBank Acc. No. CAH99602.1 (*Plasmodium berghei* str ANKA); other sequences can also be used, including AAB63302.1, XP_731015.1 and sequences having at least 80% identity to these sequences, e.g., at least 85%, 90%, or 95% identity.

Reference sequences for *gallinaceum* TRAP proteins include GenBank Acc. No. AAC47461.1 (*Plasmodium gallinaceum*); other sequences can also be used, including AAB63302.1, XP_731015.1 and sequences having at least 80% identity to these sequences, e.g., at least 85%, 90%, or 95% identity.

Reference sequences for *relictum* TRAP proteins include GenBank Acc. No. AAF00021.2 (*Plasmodium relictum*); other sequences can also be used, including AAF00021.2; ACJ24571.1; ACJ24583.1; ACJ24580.1; ACJ24578.1; ACJ24581.1; ACJ24577.1; ACJ61773.1; ACJ61772.1; ACJ24586.1; ACJ24584.1; ACJ61774.1; ACJ24582.1; AAR24260.1; ACJ24579.1; ACJ24574.1; ACJ24572.1; ACJ24576.1; ACJ24591.1; ACJ24588.1; ACJ61769.1; ACJ61770.1; ACJ61771.1; ACJ24570.1; ACJ61767.1; ACJ24575.1; ACJ24569.1; ACJ24573.1; ACJ61768.1; 1 and sequences having at least 80% identity to any of these sequences, e.g., at least 85%, 90%, or 95% identity.

Additional sequences can be identified bioinformatically, e.g., by searching databases such as GenBank, EMBL (e.g., the pathogen genome database), *P. falciparum* Genome Project Consortium; and PlasmoDB (Aurrecoechea et al. Nucleic Acids Res. 37(Database issue):D539-43 (2009); available on the internet at PlasmoDB.org).

To identify corresponding regions to a protein described herein, or to determine the percent identity of two amino acid sequences, or of two nucleic acid sequences, the sequences are aligned for optimal comparison purposes (e.g., gaps can be introduced for optimal alignment and non-homologous sequences can be disregarded for comparison purposes). In preferred embodiments, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5. An exemplary alignment of a number of Plasmodim TRAP sequences is shown in FIG. 5. This alignment was created using the Cobalt Constraint-based Multiple Protein Alignment Tool (Papadopoulos J S and Agarwala R (2007) COBALT: constraint-based alignment tool for multiple protein sequences, Bioinformatics 23:1073-79) with the following parameters:

| Exemplary Alignment Parameters | |
|---|---|
| Gap penalties | −11, −1 |
| End-Gap penalties | −5, −1 |
| CDD Parameters | |
| Use RPS BLAST | on |
| Blast E-value | 0.01 |
| Find Conserved columns and Recompute | on |

-continued

| Query Clustering Parameters | |
|---|---|
| Use query clusters | on |
| Word Size | 4 |
| Max cluster distance | 0.8 |
| Alphabet | Regular |

The antigens useful in the present application can include one or more alterations, including C55G (when using *falciparum* TRAP); removal of N-linked glycosylation sites; introduction of one or more disulfide bridges; truncation of the molecule to favor an open or closed conformation; and addition of a GPI anchor sequence to improve expression in mammalian, e.g., human, cells.

The *P. falciparum* TRAP VWA domain contains a unique cysteine residue (Cys-55) at the MIDAS region, which differs from that of all other *plasmodium* homologs that contain a conserved glycine residue at that position (see FIG. 2B). With the Cys-55 present, the *falciparum* TRAP expressed well yet easily aggregated, however, when mutated to the conserved glycine no aggregation was observed. Thus mutation of the Cys-55, e.g., to C55G, is therefore advantageous for producing *falciparum* TRAP antigen for vaccination. Other mutations can also be used, preferably conservative substitutions such as C55A and C55S. (All sequence numbering here refers to the proTRAP sequence, before cleavage of its N-terminal signal sequence).

Alternatively or in addition, it may be desirable to stabilize the TRAP protein in the closed or open state, since protective antibodies may preferentially recognize one of these 2 states. Stabilization may be obtained by one of two methods. The first method is to express a VWA domain sequence the length of which is chosen to favor the open or closed conformation. The crystal structures show that the length for the closed conformation extends from approximately residue Glu-41 to residue Lys-240 (in *falciparum* sequence) and the length for the open conformation extends from approximately residue Asn-40 to residue Val-230 (in *vivax* sequence). Thus fragments (deletion mutants) stabilized in the open or closed conformation include deletion of N-terminal and/or C-terminal residues in a *falciparum* sequence to create a TRAP fragment that is stabilized in the closed conformation comprising V47-V238; and/or deletion of N-terminal and/or C-terminal residues in a *falciparum* sequence to create a TRAP fragment that is stabilized in the open conformation comprising V47-M231; deletion of N-terminal and/or C-terminal residues in a *vivax* sequence to create a TRAP fragment that is stabilized in the closed conformation comprising amino acids V43-V234; and/or deletion of N-terminal and/or C-terminal residues in a *vivax* sequence to create a TRAP fragment that is stabilized in the open conformation comprising amino acids V43-I227. These deletion mutants can include additional amino acids on one or both ends, e.g., one, 2, 3, 4, 5, 6, 7, 8, 9, 10, 11, 12, 13, 14, 15, 16, 17, 18, 19, 20, 21, 22, 23, 24, 25, 26, 27, 28, 29, or thirty additional amino acids; for example, the deletion mutants can include all of the beta-ribbon as shown in FIGS. 6A-6B. Additional exemplary deletion mutants include open conformation deletion mutants that start at amino acid 38, 39, 40, 41, 42, or 43, and end at amino acid 227, 228, 229, 230, 231, 232, 233, 234, 235, or 236 in a *vivax* sequence (or the corresponding amino acids in the *falciparum* sequence), e.g., 40-230 (or the corresponding amino acids in the *falciparum* sequence); and closed conformation deletion mutants that start at amino acids 37, 38, 39, 40, 41, 42, or 43, and end at amino acids 234, 235, 236, 237, 238, 239, 240, 241, 242, or 243 (or the corresponding amino acids in the *falciparum* sequence), e.g., 37-234, 38-235 (or the corresponding amino acids in the *falciparum* sequence, e.g., 42-239).

The second method is to introduce a stabilizing disulfide bond into the VWA domain. To stabilize the open conformation, the disulfide is chosen to link residues that are close in the open conformation and distant in the closed conformation. Conversely, to stabilize the closed conformation, the disulfide is chosen to link residues that are distant in the open conformation and close in the closed conformation. Examples of stabilizing disulfide bonds in the open conformation are introduced by mutating to cysteine pairs of either Ser-212/Glu-218, Val-220/Ser-74 in *vivax* and Ala-216/Asn-222 or Lys-224/Gln-78 in *falciparum*. Examples of stabilizing disulfide bonds in the closed conformation are introduced by mutating to cysteine pairs of either Ser-212/Phe-226, Ile-223/Met-67, or Ile-227/Ser-74 in *vivax* and Asn-213/Ala-233, Ala-216/Phe-230, or Met-231/Gln-78 in *falciparum*. A stabilizing disulfide bond may be used with any length of protein ranging from the VWA domain to the entire TRAP protein.

TRAP protein used for immunization may be expressed in *E. coli*, other bacteria, yeast, or higher organisms. However, yeast and higher organisms add N-linked carbohydrates that obscure epitopes; such carbohydrates are not added by *Plasmodium*. Therefore, proteins expressed in the latter organisms must be mutated to remove carbohydrate addition signals. This may be achieved by mutating the N or the S/T in the carbohydrate-encoding N-X-(S/T) sequence. In a preferred embodiment, the particular mutation is chosen based on amino acids present in other *Plasmodium* species at the same position in the amino acid sequence alignment. Such mutations should also be introduced in DNA prime-boost or RNA vaccines, since these are expressed in a mammalian host. As shown herein, when the carbohydrate encoding sequence is not removed, carbohydrate addition occurs in higher organisms. Carbohydrate addition is believed to obscure important epitopes on TRAP, including the MIDAS region that is thought to be important for infection of the host.

In contrast, fucosylation on a specific Thr residue in the TSR domain marked in FIG. 5 is expected to occur in *Plasmodium*. It occurred in mammalian cells in which TRAP was expressed as shown by the crystal structure of the *vivax* form. The Thr or Ser in a CXX(S/T)CXXG sequence in TSR domains is fucosylated by POFUT2 in humans (Hofsteenge, et al., J Biol Chem. 276(9):6485-98 (2001); Tan, et al., J Cell Biol 159:373-82 (2002)). The CSVTCG (K/R)G sequence in *falciparum* and *vivax* TRAP TSR is almost identical to the CSVTCGDG sequence in TSR domain 1 of thrombospondin. The fucose is modified by addition of $\beta$1-3 glucose, by a recently identified $\beta$1-3 Glc transferase (Kozma et al., J Biol Chem. 281(48):36742-51 (2006); Sato et al., Glycobiology. 16(12):1194-206 (2006)). PSI-BLAST searches strongly suggest POFUT2 (and not POFUT1, a homologue involved in Notch fucosylation) is conserved in *P. falciparum*. Therefore, it is believed that the Thr in the TRAP TSR domain should be fucosylated in *Plasmodium*, as has been found in mammalian cells. Database searches on the $\alpha$1-3 Glc transferase are not revealing; at least a $\beta$1-3 Gal or $\beta$1-3 Glc transferase is present in *Plasmodium*.

Of particular importance for DNA/RNA vaccines, which use full-length TRAP; i.e. TRAP containing its native transmembrane and cytoplasmic domains, DNA encoding full-length TRAP, even with the N-linked site mutations and Cys-55 mutation described above, expressed poorly in human cells. However, when the transmembrane and cytoplasmic domains were exchanged for a glycosylphosphatidylinositol (GPI) anchor attachment signal sequence, the TRAP ectodomain was highly expressed on the cell surface. This has been determined using transfection of 293T cells and immunofluorescent detection of a FLAG tag attached to the N-terminus of TRAP, which has been well characterized and generally does not to influence properties of proteins to which the tag is attached.

Thus, the TRAP antigens described herein can be fusion proteins, e.g., comprising one or more mutated TRAP antigens as described herein fused to at least one non-TRAP sequence. A "non-TRAP sequence" refers to an amino acid sequence encoding a protein (or portion thereof) that is not substantially homologous to a TRAP protein, e.g., is less than 35% identical. For example, the fusion protein can include a moiety which has a high affinity for a ligand, also known as an affinity tag. For example, the fusion protein can be a GST-TRAP antigen fusion protein in which the TRAP sequence is fused to the C-terminus of the GST sequences; a polyhistidine-, e.g., 6His-, TRAP antigen in which the TRAP sequence is fused to the N- or C-terminus of a sequence encoding a polyhistidine tag; or a FLAG-TRAP fusion protein in which the TRAP sequence is fused to one or more FLAG sequences (e.g., N-AspTyrLysAspAspAspAsp-Lys-C; SEQ ID NO:14). Such fusion proteins can facilitate the purification of recombinant TRAP antigen.

In some embodiments, the non-TRAP sequence can be a carrier or adjuvant. These can include FLAGELLIN proteins (see, e.g., Bargieri et al., Journal of Parasitology Research Volume 2011 (2011), Article ID 965369; doi:10.1155/2011/965369), a Hepatitis B virus-derived surface antigen, e.g., core antigen (see, e.g., Francis et al., Proc. Natl. Acad. Sci. USA 87:2545-2549 (1990)) or small hepatitis B virus surface protein (HBs) (see, e.g., Wunderlich et al., Infection and Immunity 68 (10): 5839 (2000); Stoute et al., N Engl J Med. 336:86-91 (1997); Bojang et al., Lancet, 358(9297) 1927-1934(2001)). In some embodiments, the non-TRAP sequence comprises one or more CpG motifs (e.g, Krieg et al., Trends Microbiol. 1998 January; 6(1):23-7; Sato et al., Science. 1996 Jul. 19; 273(5273):352-4).

Alternatively or in addition, the fusion protein can be a TRAP protein containing a heterologous signal sequence at its N-terminus. In certain host cells (e.g., mammalian host cells), expression and/or secretion of TRAP can be increased through use of a heterologous signal sequence that is from the same species as the host cell.

Fusion proteins can also include all or a part of a serum protein, e.g., an IgG constant region, or human serum albumin.

In some embodiments, the fusion protein further comprises a sequence that allows cleavage and thus removal of the non-TRAP sequences, e.g., a protease recognition site (proteolytic cleavage site) that would allow removal of any non-TRAP sequences, e.g., after purification. Alternatively, proteases such as DAPase, which removes dipeptides sequentially from the N-terminus of purified His-tagged proteins until it reaches an engineered or intrinsic stop point (i.e., a glutamine residue acts as a DAPase stop point), can be used.

Purified TRAP antigen proteins can be used in a number of clinical and research settings. For example, the proteins can be used in *Plasmodium* infectivity assays, (e.g., as known in the art), or to generate antibodies specific for TRAP antigens; such antibodies can then be administered as therapeutics, e.g., to subjects who have or are at risk of contracting malaria. In addition, a TRAP antigen can be administered to a subject who has or is at risk of contracting malaria, e.g., a subject who resides in or may visit a geographic area in which malaria is endemic, or who is in contact with an individual who has malaria or who resides in or may visit a geographic area in which malaria is endemic, e.g., health care workers, to elicit an anti-TRAP immune response, e.g., the production of anti-TRAP antibodies, that is expected to result in immunity to, or reduced risk of, malarial infection.

Nucleic Acids, Recombinant Expression Vectors, Host Cells and Genetically Engineered Cells In one aspect, the invention provides nucleic acid molecules that encode a TRAP antigen or fusion protein as described herein.

In another aspect, the invention includes vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a TRAP antigen nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., TRAP antigens and fusion proteins, and the like).

The recombinant expression vectors of the invention can be designed for expression of TRAP antigens in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

One strategy to maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The TRAP antigen expression vector can be, e.g., a yeast expression vector; a vector for expression in insect cells, e.g., a baculovirus expression vector; or a vector suitable for expression in a mammalian host or mammalian cells, e.g., a viral or plasmid vector.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) Cell 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Mammary-gland specific promoters are particularly useful for producing the TRAP antigens in the milk of a transgenic animal, e.g., a goat or cow.

In another aspect the invention provides a host cell which includes a nucleic acid molecule described herein, e.g., a TRAP antigen nucleic acid molecule within a recombinant expression vector or a TRAP antigen nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a TRAP antigen can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a TRAP antigen. Accordingly, the invention further provides methods for producing a TRAP antigen using the host cells of the invention. In one embodiment, the method includes culturing the host cell of the invention (into which a recombinant expression vector encoding a TRAP antigen has been introduced) in a suitable medium such that a TRAP antigen is produced. In another embodiment, the method further includes isolating a TRAP antigen from the medium or the host cell using methods known in the art.

The invention also provides non-human transgenic animals. Such animals are useful, e.g., for studying the function and/or activity of a TRAP antigen and for producing TRAP antigen, e.g., in the milk of the animal. As used herein, a "transgenic animal" is a non-human animal, preferably a mammal, e.g., a rodent (such as a rat or mouse) or a ruminant such as a cow, goat or sheep, in which one or more of the cells of the animal includes a transgene expressing a TRAP antigen as described herein, which preferably is integrated into or occurs in the genome of the cells of a transgenic animal. A TRAP antigen transgene directs the expression of an encoded gene product in one or more cell types or tissues of the transgenic animal. Thus, a transgenic animal can be one in which a TRAP antigen transgene DNA molecule has been introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a TRAP antigen transgene to direct expression of the TRAP antigen to particular cells. A transgenic founder animal can be identified based upon the presence of a TRAP antigen transgene in its genome and/or expression of TRAP antigen mRNA in tissues or cells of the animals. A transgenic founder animal can then be used to breed additional animals carrying the transgene. Moreover, transgenic animals carrying a transgene encoding a TRAP antigen can further be bred to other transgenic animals carrying other transgenes.

In some embodiments the TRAP antigen transgene is under the control of a tissue specific promoter, e.g., a milk or egg specific promoter, and recovered from the milk or eggs produced by the animal. Suitable animals are mice, chickens, pigs, cows, goats, and sheep.

The invention also includes a population of cells from a transgenic animal expressing a TRAP antigen transgene.

The TRAP antigen-encoding nucleic acid can be a nucleic acid vaccine, e.g., as described in Hoffman et al., "Using DNA based vaccine technology and the Malaria Genome Project to overcome obstacles to Malaria vaccine development." In: Sherman, editor. *Malaria: parasite biology, pathogenesis and protection.* Washington, D.C.: ASM Press; 1998. pp. 73-91; Krieg et al., Trends Microbiol. 1998 January; 6(1):23-7;

Methods of Eliciting an Immune Response

Also provided herein are methods of eliciting an immune response, i.e., the production of anti-TRAP antibodies, in a subject, e.g., a subject who has or is at risk of contracting malaria, e.g., a subject who resides in or may visit a geographic area in which malaria is endemic, or who is in contact with an individual who has malaria or who resides in or may visit a geographic area in which malaria is endemic, e.g., health care workers. Although human subjects can be treated by the methods described herein, other subjects can also include veterinary or livestock subjects who are susceptible to malaria, e.g., primates.

The methods of eliciting an immune response (also referred to herein as immunization) include administering a TRAP antigen protein or TRAP antigen-encoding nucleic acid as described herein.

Methods of immunizing with proteins and nucleic acids are well known in the field. For example, methods for prime and boost vaccines against TRAP have been disclosed in which TRAP is encoded as a DNA sequence in vectors such as adenovirus for the prime and a different vector such as a poxvirus for the boost (Hill et al. Hum Vaccin 6:78-83 (2010)). As described herein, immunization with TRAP proteins lacking N-linked glycans and encoding either the VWA, elastic ribbon, and/or TSR domains, or the entire extracellular domain, elicits high—titer antibodies in mice and rabbits.

The methods can include administering one or more doses of the TRAP antigen or TRAP antigen-encoding nucleic acid, e.g., a prime dose and one or more booster doses. The methods can further include administration of an adjuvant, e.g., a compound that enhances the longevity, potency, and/or quality of the specific immune response to TRAP antigen, and preferably has no or minimal toxicity or long-lasting immune effects on its own. Adjuvants can include, for example, mineral salt adjuvants (e.g., alum-based); tensoactive adjuvants (e.g., saponins); polymeric microspheres (e.g., poly (DL-lactide-coglycolide) microspheres); bacteria-derived adjuvants (e.g., N-acetyl muramyl-L-alanyl-D-isoglutamine (MDP)); liposome adjuvants; adjuvant emulsions (e.g., oil in water or water in oil emulsions such as FIA, Montanide, Adjuvant 65, and Lipovant); cytokines (e.g., IFN-gamma or GM-CSF); and carbohydrate adjuvants (e.g., inulin), among others. The choice of adjuvant can be determined by the nature of the antigen (e.g., protein or nucleic acid) and the route of administration (e.g., parenteral or mucosal). See, e.g., Petrovsky and Aguilar, Immunology and Cell Biology (2004) 82, 488-496; Kenney and Edelman, Expert Rev Vaccines. 2003 April; 2(2):167-88; Coler et al., Parasite Immunol. 2009 September; 31(9):520-8; and Reed et al., Trends Immunol. 2009 January; 30(1):23-32. In some embodiments, the adjuvants include an oil in water emulsion, monophosphoryl lipid A and the saponin derivative QS21 (Stoute et al., J Infect Dis. 178 (4):1139-1144 (1998)).

In some embodiments, the methods described herein elicit sterilizing immunity in a mammal that kills sporozoites either before infection of the liver, or during development in liver cells, before merozoites are released and begin the erythrocytic stage of the *Plasmodium* life cycle.

In some embodiments, the methods described herein elicit antibody titers of over 1,000, e.g., over 10,000, or over 100,000, in an immunized subject.

Pharmaceutical Compositions and Methods of Administration

The TRAP antigens and TRAP antigen-encoding nucleic acids described herein can be incorporated into pharmaceutical compositions. Such compositions typically include the antigen or nucleic acid (i.e., as an active agent) and a pharmaceutically acceptable carrier. As used herein, "pharmaceutically acceptable carriers" includes saline, solvents, dispersion media, coatings, antibacterial and antifungal agents, isotonic and absorption delaying agents, and the like, compatible with pharmaceutical administration. In some embodiments, the pharmaceutical compositions include an adjuvant as known in the art and/or described herein.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

For administration by inhalation, the compounds are typically delivered in the form of an aerosol spray from pressured container or dispenser which contains a suitable propellant, e.g., a gas such as carbon dioxide, or a nebulizer. Such methods include those described in U.S. Pat. No. 6,468,798.

Pharmaceutical compositions comprising TRAP antigen-encoding nucleic acids can be administered by any method suitable for administration of nucleic acid agents, such as DNA vaccines. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the pharmaceutical compositions include carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

Dosage, toxicity and therapeutic efficacy of the TRAP antigens can be determined by standard vaccine testing procedures in experimental animals or clinical trials, e.g., for determining the LD50 (the dose lethal to 50% of the population) and the ED50 (the dose therapeutically effective in 50% of the population). The methods generally include administering at least one dose of the TRAP antigen to a subject (e.g., test animal or human clinical trial subject), optionally followed after a period of time by one or more boost doses, and then protection from challenge by an appropriate *Plasmodium* organism is measured. The organism challenge can be performed by injecting sporozoites collected from the salivary gland of mosquitoes, or by letting infected mosquitoes bite animals. This (biting) is also done routinely with humans in clinical trials; a well-defined strain of *falciparum* such as 3D7 is typically used, which gives a chloroquine-treatable infection in case protection is not achieved.

The data obtained from the animal studies can be used in formulating a range of dosage for use in humans, which is then confirmed in clinical trials, e.g., as described above. The dosage will lie preferably within a range of concentrations that include the ED50 with little or no toxicity. The dosage may vary within this range depending upon the dosage form employed (e.g., TRAP antigen protein or nucleic acid) and the route of administration utilized. A dose may be formulated in animal models to achieve a desired level of protection without significant toxicity. Such information can be used to determine useful starting doses in humans for clinical trials.

A therapeutically effective amount of a TRAP antigen (i.e., an effective dosage) as described herein depends on the form selected, e.g., whether TRAP antigen protein or TRAP-antigen-encoding nucleic acid (e.g., a DNA vaccine) is used. The skilled artisan will appreciate that certain factors may influence the dosage and timing required to effectively elicit an immune response in a subject, including but not limited to previous treatments and the general health and/or age of the subject. Moreover, treatment of a subject with a therapeutically effective amount of the TRAP antigens described herein can include a single dose or a series of treatments (i.e., a priming dose and one or more boosts).

The TRAP antigens can be included in a kit, container, pack, or dispenser, optionally with instructions for administration, for use in a method described herein.

EXAMPLES

The invention is further described in the following examples, which do not limit the scope of the invention described in the claims.

Example 1

Structural Features of TRAP Domains

Both the TSR and VWA domains are responsible for TRAP's adhesion to liver cells, but the exact mechanism is not clear. Both adhesive domains show affinity for heparin, and the TSR domain binds to heparin sulfate proteoglycans on the hepatocyte surface. However, the VWA domain has at least one other unidentified hepatocyte ligand (Akhouri et al., 2004; McCormick et al., 1999; Muller et al., 1993). Interestingly, surface plasmon resonance analysis of TRAP-heparin binding suggests a two-state reaction with conformational change (Akhouri et al., 2004). Although there is a solution NMR structure for the TSR domain, this does not show how it might fold in tandem with the VWA domain on the parasite surface (Tossavainen et al., 2006). Recently, a crystal structure was solved for the VWA domain of *Toxoplasma gondii* Micronemal protein 2 (MIC2), a member of the TRAP protein family (Tonkin et al., 2010). However, the VWA domain used for that structure had substantial truncation at the C-terminus, including two predicted alpha-helices and one predicted beta-strand. Several subfamilies of VWA domains undergo conformational change that regulates affinity for ligand (Springer, 2006).

Figure 2A:
FIG. 2A is an illustration of the N-terminal portion of an exemplary *P. falciparum* TRAP sequence (amino acids 1-263 of SEQ ID NO:1). Disulfide bonds are illustrated by shaded bars.

In the sequence of TRAP, one cysteine each is present in two short segments between the signal sequence and the VWA domain, and between the VWA and TSR domains (FIG. 2A). It was hypothesized that these cysteines are linked in a disulfide bond (shaded in light gray in FIG. 2A), and that the insertion of the VWA domain between these short, disulfide-linked segments creates a similar linkage as in integrins and selectins, enabling similar pivoting and mechanochemical activation of ligand binding by the sporozoite's cytoskeleton. Mechanochemical transmission of information between the ligand binding site and the cytoplasmic domain could thus guide gliding motility. The structure of the two adhesive domains in TRAP should also reveal the basis for ligand recognition by the VWA domain.

The cysteines that are hypothesized to link the segments N and C-terminal of the VWA domain are conserved in all *Plasmodium* species (FIG. 2B). The DXSXS motif, which binds to a $Mg^{2+}$ ion in other VWA domains where the $Mg^{2+}$ coordinates an acidic residue in the ligand, is also conserved (FIGS. 2A-2B). A cysteine in the DXSXS motif in *P. falciparum* is not conserved in other *Plasmodium* species and thus was not expected to be disulfide-bonded (FIG. 2B).

Based on the above considerations, a DNA segment encoding the murine Ig chain signal peptide, *falciparum* TRAP adhesive domains (26-299 with unconserved Cys in the MIDAS mutated to Ala and N-link site mutated to Ser) and a HHHHHHA sequence was cloned into the EcoR I and NotI sites of plasmid pLEXm (Aricescu et al., Acta Crystallogr D Biol Crystallogr 62, 1243-1250 (2006)); this construct was termed "TRAP6", and includes the sequence of TRAP from the predicted N-terminal residue after signal-peptide cleavage to after the TSR domain. Site-directed mutagenesis was used to mutate the unconserved cysteine in the DXSXS motif to glycine and remove the potential N-linked glycosylation site. The nucleic acid sequence was as follows:

TRAP-6

(SEQ ID NO: 16)
ATGGATATGAGAGTTCCTGCTCAATTGCTGGGGTTGCTCTTGCTCTGGTTCAGTGGGGTGTTGGGG

AGGGATGTGCAGAATAACATTGTGGACGAGATCAAGTACCGCGAGGAGGTATGCAATGACGAGGTGGATTTGTATCTCTTG

ATGGATGGCTCCGGATCGATCAGGAGGCACAACTGGGTCAATCATGCGGTCCCCCTGGCCATGAAGCTGATCCAGCAGCTG

AATCTCAACGACAATGCCATTCACCTCTATGCCAGCGTGTTCTCAAACAACGCGAGAGAGATCATCCGCTTGCACAGCGAC

GCTTCGAAGAACAAGGAAAAGGCACTCATCATTATCAAATCGTTGCTCTCAACGAATCTTCCGTACGGTAAAACGTCATTG

-continued

```
ACCGACGCACTGTTGCAAGTCCGCAAACATCTGAACGATAGAATCAACCGCGAGAATGCGAATCAGCTTGTAGTAATCCTG

ACGGACGGTATTCCCGATTCGATTCAAGATTCACTCAAGGAAAGCAGGAAACTTTCAGACAGAGGCGTGAAAATCGCTGTG

TTTGGAATTGGTCAGGGAATCAACGTGGCATTCAACAGGTTCCTGGTCGGTTGTCACCCCTCCGATGGAAAATGCAATCTC

TACGCGGACTCAGCGTGGGAAAACGTCAAGAACGTGATCGGACCCTTTATGAAAGCCGTCTGTGTCGAGGTAGAGAAACC

GCGTCGTGTGGAGTGTGGGATGAGTGGTCACCGTGCTCCGTCACGTGCGGAAAAGGAACTAGGAGCCGCAAGAGGGAGATC

CTTCACGAAGGCTGCACATCGGAGTTGCAAGAGCAGTGTGAAGAAGAGAGGTGCCTCCCGAAGCGCGAACCTCTTGACG

TACCGGATGAACCAGCGCATCACCATCACCATCACGCG
```

The underlined sequence is a murine Ig chain signal peptide, and the double underlined sequence encodes the 6His tag. The protein sequence is as follows; mutated residues are bold and double underlined, and the TSR domain is underlined.

TRAP6
SEQ ID NO: 1
RDVQNNIVDEIKYREEVCNDEVDLYLLMDGSGSIRRHNWVNHAVPLA

MKLIQQLNLNDNAIHLYASVFSNNAREIIRLHSDASKNKEKALIIIK

SLLSTNLPYGKTSLTDALLQVRKHLNDRINRENANQLVVILTDGIPD

SIQDSLKESRKLSDRGVKIAVFGIGQGINVAFNRFLVGCHPSDGKCN

LYADSAWENVKNVIGPFMKAVCVEVEKTASCGVWDEWSPCSVTCGKG

TRSRKREILHEGCTSELQEQCEEERCLPKREPLDVPDEP

The sequence also included a 6His tag (AHHHHHHA; SEQ ID NO:3) at the N terminus HEK293S GnTI- cells (Reeves et al., Proceedings of the National Academy of Sciences of the United States of America 99, 13419-13424 (2002))) were transiently transfected by using polyethylenimine. Culture supernatants (1 L) were harvested after 5 days. Purification was performed with Ni-NTA affinity followed by Superdex 5200 column equilibrated with 20 mM HEPES 7.2 and 300 mM NaCl. The purified protein was concentrated to about 5 mg/ml and stored at −80° C. Crystallization screening was done with a Mosquito robot using commercially available sparse matrix screens. Diffraction-quality crystals were produced at 4° C. in a mother liquor solution containing 0.1 M Tris 8.5, 0.2 M Li2SO4, 25% PEG4000. Single crystals were frozen in liquid nitrogen prior to X-ray diffraction testing and data collection. Diffraction data were collected at 100 K at beamline 23-ID, Advanced Photon Source, Argonne National Laboratory. Early molecular replacement attempts using different VWA domains or TSR domains as models failed. The solution was obtained using molecular replacement a modified VWA domain of human capillary morphogenesis protein 2 (pdb ID 1shu) as model. The crystal characteristics are shown in Table 1.

TABLE 1

TRAP crystal X-Ray diffraction data and refinement -
I4 spacegroup pfTRAP (26-299)

| | |
|---|---|
| Space group | I4 |
| Cell dimensions | |
| a, b, c (Å) | 110.2, 110.2, 47.0 |
| α, β, γ (°) | 90.00, 90.00, 90.00 |
| Resolution (Å) | 43.27-2.20 (2.26-2.20) |
| $R_{sym}$ | 16.5% (112.3%) |
| $I/sI$ | 11.26 (1.69) |

TABLE 1-continued

TRAP crystal X-Ray diffraction data and refinement -
I4 spacegroup pfTRAP (26-299)

| | |
|---|---|
| Completeness (%) | 98.1% (97.5%) |
| Redundancy | 2.89 (2.80) |
| No. reflections | 14268 |
| $R_{work}/R_{free}$ | 17.6%/22.3% |
| No. atoms | |
| Protein | 1584 |
| Water | 117 |
| B-factors | |
| Protein | 50.37 |
| Water | 51.01 |
| R.m.s deviations | |
| Bond lengths (Å) | 0.008 |
| Bond angles (°) | 1.10 |

Figure 3:
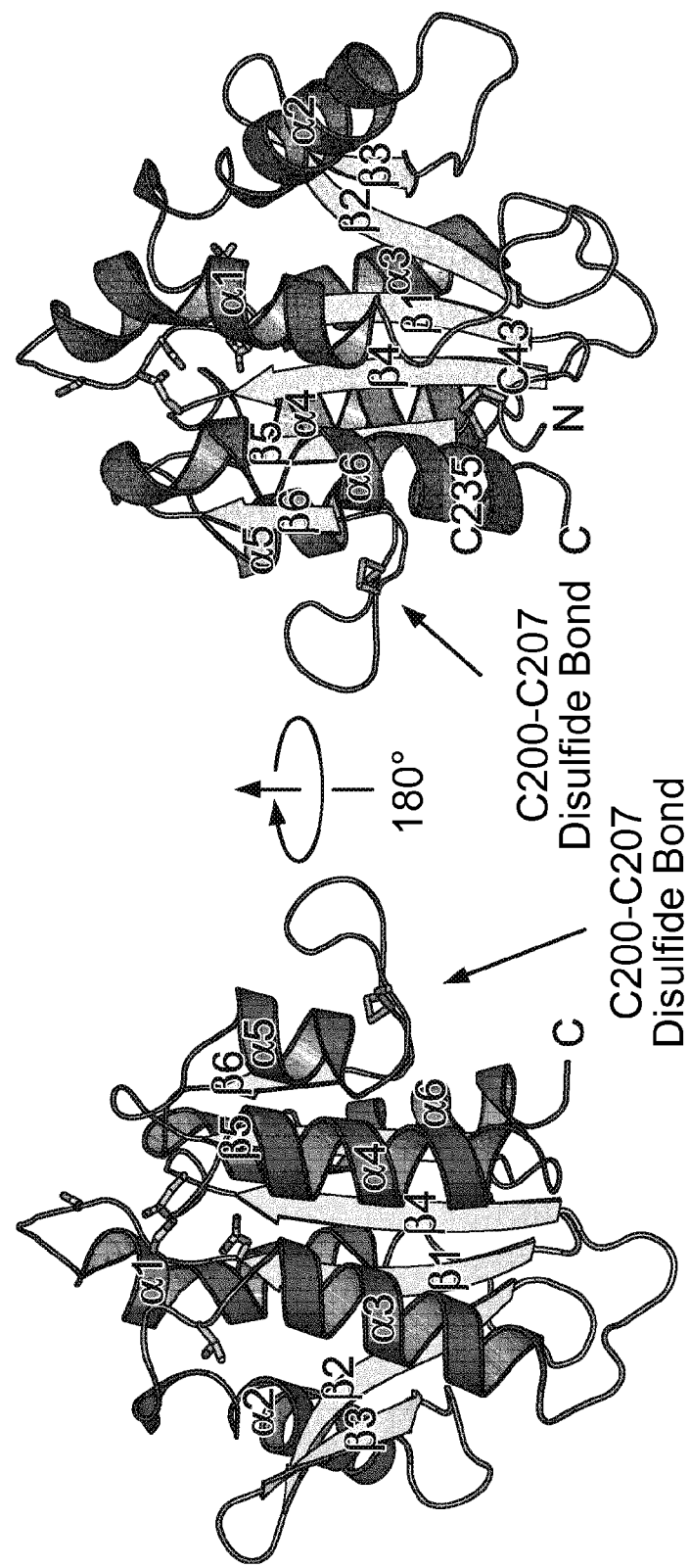
FIG. 3 is an illustration of the overall structure of *P. falciparum* TRAP VWA domain. The MIDAS residues are shown as sticks. The cysteine side chain bonds are labeled. Secondary structure elements are also labeled.
Figure 7A:
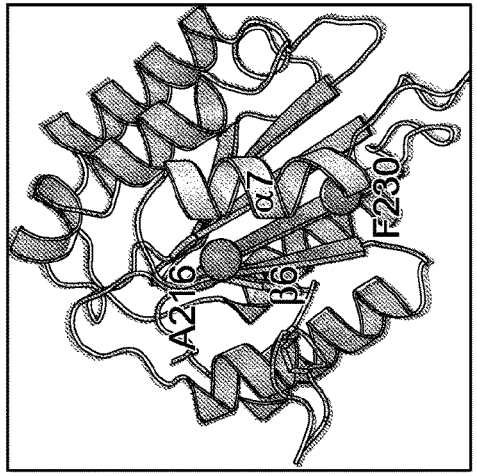
Figure 7B:
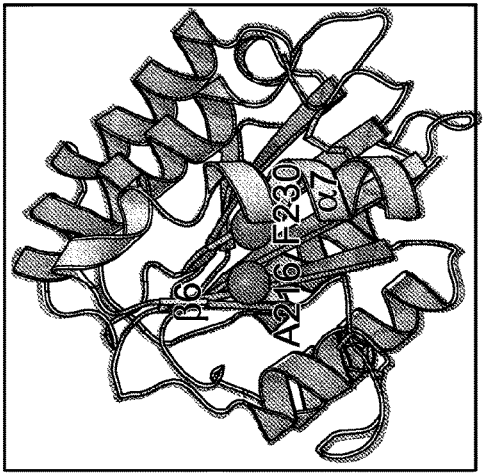
Figure 7C:
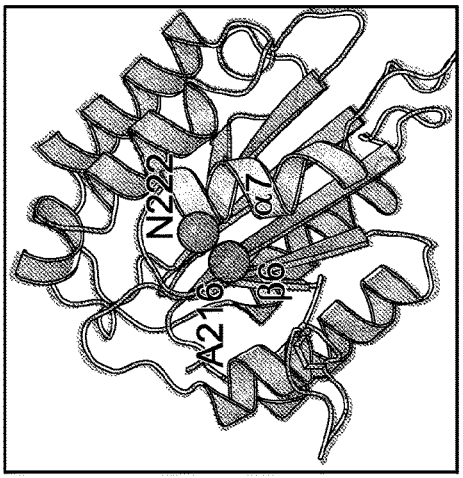
Figure 7D:
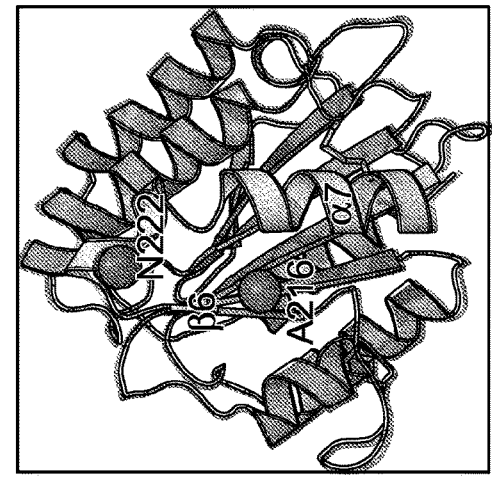

TRAP VWA fold superficially resembles the typical VWA fold with 6β-strands surrounded by 6 α-helices (see FIG. 3), but differs from other VWA or integrin I domain structures in its unusual MIDAS. A long range disulfide links the sequence N-terminal to the VWA to the final C-terminal VWA domain α6-helix, and the α6-helix is longer than usual. The other disulfide bond residues, C205 and C212, are conserved within *plasmodium* species. However, they are absent in other VWA domains.

In addition, a construct comprising the *P. vivax* TRAP adhesive domains (25-283) was expressed and purified using similar procedures. That construct had the following sequence:

P. vivax TRAP
SEQ ID NO: 15
DEKVVDEVKYSEEVCNEQVDLYLLVDGSGSIGYPNWITKVIPMLNGLINS

LSLSRDTINLYMNLFGSYTTELIRLGSGQSIDKRQALSKVTELRKTYTPY

GTTSMTAALDEVQKHLNDRVNREKAIQLVILMTDGVPNSKYRALEVANKL

KQRNVRLAVIGIGQGINHQFNRLIAGCRPREPNCKFYSYADWNEAVALIK

PFIAKVCTEVERVANCGPWDPWTACSVTCGRGTHSRSRPSLHEKCTTHMV

SECEEGECP

The protein was crystallized with 15% PEG20000 and 0.1 M Tris 8.5. Crystals were harvested in their mother liquor supplemented with 20% glycerol as cryoprotectant, then flash frozen in liquid nitrogen. The data was collected and the structure was solved using the VWA domain of human capillary morphogenesis protein 2 as search model.

A model is shown in FIGS. 4A-B. Interestingly, the two short segments from the two ends of VWA domain form anti-parallel 13 strands, termed "Elastic β-ribbon" here.

Partial residues in this Elastic ribbon were derived from the C-terminal α-helix in the *falciparum* VWA structure. The structure of the *P. Vivax* VWA domain showed that it was in an open conformation even in the absence of a metal ion or pseudo-ligand. Both Mg and Mn could be soaked into the crystal and bound to the MIDAS with no conformational change of the VWA domain. The structure of the TSR domain shows it belongs to the group 2 according the disulfide bond pattern. A disaccharide, Glcβ1,3 Fuc was O-linked to the Thr in the CSVTCG sequence motif on the TSR domain.

A comparison of the structures of the *falciparum* and *vivax* A domains was revealing. Comparison between the two TRAP structures, and to integrin I domains, showed that the *falciparum* protein crystallized in the closed conformation of the VWA or I domain, whereas the *vivax* protein crystallized in the open conformation. C-terminal, axial displacement of the α6-helix in the open compared to the closed conformation was coupled to reshaping of the b6-a7 loop, and movement of a Trp in this loop, similar to a Phe residue in integrins. N-C terminal disulfide bonds and position of terminal residues (K240 in *falciparum* and 8236 in *vivax*) were also shifted relative to each other.

The influence of lattice contact on the *falciparum* VWA structure was evaluated. In the the 14 space group pfTRAP, the unusual MIDAS is adjacent to the lattice contact area, and probably perturbed by lattice contact; this is not seen in the P4212 spacegroup pfTRAP. The MIDAS residues are conserved within species, and mutation of two of them has been found to inhibit TRAP function Matuschewski et al., EMBO J. 21, 1597-1606 (2002)). The specific binding of A domain to HepG2 cells is divalent cation dependent (Jethwaney et al., Infect Immun 73, 5883-5891 (2005)). In contrast, the β6-α6 loop and α6-helix in the closed TRAP conformation were not in lattice contacts, and thus their configuration, which is similar to that in closed integrin I domains, strongly suggests that the *falciparum* TRAP structure represents the closed conformation of TRAP (which should be accessible to TRAP in any *Plasmodium* species), Superimposition of *vivax* TRAP with both open and closed conformations of integrin aM I domains showed marked similarity to the open conformation of integrin I domains, both in the b6-a6 loop and a6-helix, and in the loops surrounding the MIDAS. Furthermore, the TRAP MIDAS adopts the open conformation, with the Mg ion in direct coordination with the Thr and not the Asp of the MIDAS. Taken together these results indicate that the *falciparum* and *vivax* structures represent two different conformations: closed and open, respectively.

Example 2

Generation of Anti-Trap Antibodies

Immunization of mice with irradiated sporozoites results in production of antibodies and cytotoxic T-cells against TRAP Immunization with small fragments of TRAP alone provides no or at best partial protection (Gantt et al., Infect. Immun 68(6):3667-3673 (2000)), but complete protection has been documented in mice immunized with a mixture of transfectants expressing CSP and TRAP (Khusmith et al., 2001).

To determine whether immunization of animals with the TRAP peptides described would produce an immune response, *falciparum* TRAP6 (26-299, including the A domain and TSR and 12 residues extended at the C-terminus) and TRAPF (26-511, including the A domain, TSR, and repeats) were prepared for immunization. The nucleic acid and protein sequences of TRAPF, with the non-conserved cysteine in the DXSXS motif mutated to glycine and the potential N-linked glycosylation sites removed, is as follows:

```
TRAP-F
ATGGATATGAGAGTTCCTGCTCAATTGCTGGGGTTGCTCTTGCTCTGGTTCAGTGGGGTGTTGGGG

AGGGATGTGCAGAATAACATTGTGGACGAGATCAAGTACCGCGAGGAGGTATGCAATGACGAGGTGGATTTGTATCTCTTG

ATGGATGGCTCCGGATCGATCAGGAGGCACAACTGGGTCAATCATGCGGTCCCCCTGGCCATGAAGCTGATCCAGCAGCTG

AATCTCAACGACAATGCCATTCACCTCTATGCCAGCGTGTTCTCAAACAACGCGAGAGAGATCATCCGCTTGCACAGCGAC

GCTTCGAAGAACAAGGAAAAGGCACTCATCATTATCAAATCGTTGCTCTCAACGAATCTTCCGTACGGTAAAACGTCATTG

ACCGACGCACTGTTGCAAGTCCGCAAACATCTGAACGATAGAATCAACCGCGAGAATGCGAATCAGCTTGTAGTAATCCTG

ACGGACGGTATTCCCGATTCGATTCAAGATTCACTCAAGGAAAGCAGGAAACTTTCAGACAGAGGCGTGAAAATCGCTGTG

TTTGGAATTGGTCAGGGAATCAACGTGGCATTCAACAGGTTCCTGGTCGGTTGTCACCCCTCCGATGGAAAATGCAATCTC

TACGCGGACTCAGCGTGGGAAAACGTCAAGAACGTGATCGGACCCTTTATGAAAGCCGTCTGTGTCGAGGTAGAGAAAACC

GCGTCGTGTGGAGTGTGGGATGAGTGGTCACCGTGCTCCGTCACGTGCGGAAAAGGAACTAGGAGCCGCAAGAGGGAGATC

CTTCACGAAGGCTGCACATCGGAGTTGCAAGAGCAGTGTGAAGAAGAGAGGTGCCTCCCGAAGCGCGAACCTCTTGACGTA

CCGGATGAACCAGAGGACGACCAGCCAAGGCCCAGAGGAGACAACTTCGCCGTAGAAAAACCCAACGAGAACATCATTGAC

AACAACCCTCAAGAACCCTCGCCGAATCCCGAAGAGGGAAAGGGTGAAAATCCTAATGGTTTTGATTTGGATGAGAATCCC

GAGAATCCTCCGAACCCTCCCAACCCTCCGAATCCCCCGAATCCACCCAATCCACCTAATCCGGATATCCCGGAACAAGAG

CCGAACATTCCCGAAGATTCGGAGAAGGAAGTCCCCTCGGACGTCCCGAAGAATCCGGAGGACGATAGGGAGGAAAACTTT

GACATTCCCAAAAAGCCCGAGAACAAGCATGATAATCAGAACAACCTTCCAAATGACAAGTCCGATCGCTACATCCCCTAT

TCGCCGCTCAGCCCTAAAGTACTGGATAACGAGCGCAAACAGTCAGATCCCCAGAGCCAGGACAATAACGGCAATAGACAC
```

```
GTACCGAACTCGGAGGACAGAGAGACTAGGCCACACGGAAGAAACAATGAGAATAGAAACTACAATCGCAAGCATTCGAAT

ACACCGAAACATCCCGAAAGAGAAGAACACGAGAAACCGGACAACAACAAGAAGAAAGCGGGTAGCGATAACAAGTATAAG
```

<u>GCGCATCACCATCACCATCACGCG</u>

The underlined nucleic acid sequence encodes a murine Ig chain signal peptide, the dotted underlined region is the VWA domain, and the double underlined sequence encodes the 6His tag.

```
TRAPF (Full ectodomain)
                                                SEQ ID NO: 2
RDVQNNIVDEIKYREEVCNDEVDLYLLMDGSGSIRRHNWVNHAVPLA

MKLIQQLNLNDNAIHLYASVFSNNAREIIRLHSDASKNKEKALIIIK

SLLSTNLPYGKTSLTDALLQVRKHLNDRINRENANQLVVILTDGIPD

SIQDSLKESRKLSDRGVKIAVFGIGQGINVAFNRFLVGCHPSDGKCN

LYADSAWENVKNVIGPFMKAVCVEVEKTASCGVWDEWSPCSVTCGKG

TRSRKREILHEGCTSELQEQCEEERCLPKREPLDVPDEPEDDQPRPR

GDNFAVEKPNENIIDNNPQEPSPNPEEGKGENPNGFDLDENPENPPN

PPNPPNPPNPPNPNPDIPEQEPNIPEDSEKEVPSDVPKNPEDDREE

NFDIPKKPENKHDNQNNLPNDKSDRYIPYSPLSPKVLDNERKQSDPQ

SQDNNGNRHVPNSEDRETRPHGRNNENRNYNRKHSNTPKHPEREEHE

KPDNNKKKAGSDNKYK
```

The sequence also included a 6His tag (AHHHHHHA; SEQ ID NO: 3) at the N terminus The proteins were expressed in HEK 293S GnTI– cells, and purified by Ni-NTA affinity. The buffer was then changed to PBS, and proteins were concentrated to 1.46 mg/ml (TRAP6) and 2.2 mg/ml (TRAPF). Both rabbits and mice were used for immunization.

The rabbits were immunized by Cocalico Biological, Inc (Reamstown, Pa.) under an IACUC approved standard 90-day protocol, with 2 rabbits for each antigen given an initial inoculation and four boosts. A pre-bleed, two test bleeds, and a product bleed were taken (about 100 ml from each rabbit).

An ELISA assay was used to test the antisera. The TRAPF antigen was coated at 2 ug/ml, blocked with BSA, then incubated with the antisera. Binding was detected with HRP-anti-rabbit antibodies, developed with HRP substrate. Absorbance was read using an ELISA plate reader. The results are shown in Table 2.

TABLE 2

| rabbit dilution | Pre-immune | Test 1 (11/18) | Test 2 (12/8) | Pre-immune | Test 1 (11/18) | Test 2 (12/8) |
|---|---|---|---|---|---|---|
| | IMDI3 (TRAP-FL ecto) | | | IMDI4 (TRAP-FL ecto) | | |
| 1:125,000 | 0.000 | 0.363 | 0.634 | 0.000 | 0.220 | 0.605 |
| 1:25,000 | 0.000 | 1.003 | 1.334 | 0.000 | 0.738 | 1.446 |
| 1:5,000 | 0.015 | 1.619 | 1.689 | 0.006 | 1.528 | 1.768 |
| 1:1,000 | 0.071 | 1.662 | 1.713 | 0.024 | 1.860 | 1.882 |
| | IMDI5 (TRAP-short) | | | IMDI6 (TRAP-short) | | |
| 1:125,000 | 0.000 | 0.319 | 0.367 | 0.000 | 0.256 | 0.456 |
| 1:25,000 | 0.149 | 1.032 | 1.143 | 0.000 | 0.927 | 1.196 |
| 1:5,000 | 0.005 | 1.605 | 1.598 | 0.002 | 1.415 | 1.585 |
| 1:1,000 | 0.028 | 1.806 | 1.811 | 0.009 | 1.693 | 1.698 |

There were good titers in Elisa (at 1:125,000) for all 4 animals; an increase was observed in the second test bleeds. All 4 antisera worked in immunoprecipitation and Western blot experiments using cell lysate from TRAP-transfected cells.

Mice were also immunized with the same antigens to generate monoclonal antibodies. 3 CBF1 mice were immunized with each antigen (TRAP6 and TRAPF). Three IP immunizations were administered; the 1st injection was with complete Freund's adjuvant, the 2nd and 3rd with incomplete Freund's adjuvant. On day 38 tail bleeds were taken and tested by ELISA. The results are shown in Table 3.

TABLE 3

| | | antigen | | | | | | | |
|---|---|---|---|---|---|---|---|---|---|
| | | Irrelevant protein | | | TRAP-F animal # | | | TRAP-6 (short) | | |
| | | 1 | 2 | 3 | 4 | 5 | 6 | 7 | 8 | 9 |
| serum dilution | 1:25,000 | 0 | 0 | 0 | 0.877 | 0.969 | 0.618 | 0.660 | 0.148 | 0.595 |
| | 1:5,000 | 0 | 0 | 0 | 1.262 | 1.223 | 0.871 | 1.000 | 0.421 | 1.137 |
| | 1:1000 | 0 | 0 | 0 | 1.471 | 1.550 | 1.289 | 1.206 | 0.960 | 1.440 |

Again, there were good titres (1:25,000).

These results demonstrate that administration of these antigens can elicit the production of TRAP-specific antibodies in mammals.

Example 3

Expression of Full-Length TRAP in Mammalian Cells

The following experiments describe methods to express full-length TRAP; i.e. TRAP containing its native transmembrane and cytoplasmic domains in mammalian cells. Full-length TRAP, even with the N-linked site mutations and Cys-55 mutation described above, cannot be expressed in human cells. Thus a construct was made wherein the transmembrane and cytoplasmic domains were exchanged for a glycosylphosphatidylinositol (GPI) anchor attachment signal sequence. The sequence of this construct was as follows:

```
Flag-TRAP-GPI
                                          SEQ ID NO: 4
MDMRVPAQLLGLLLLWFPGSRSLDYKDDDDKGSGRDVQNNIVDEIKY

REEVCNDEVDLYLLMDGSGSIRRHNWVNHAVPLAMKLIQQLNLNDNA

IHLYASVFSNNAREIIRLHSDASKNKEKALIIIKSLLSTNLPYGKTS

LTDALLQVRKHLNDRINRENANQLVVILTDGIPDSIQDSLKESRKLS

DRGVKIAVFGIGQGINVAFNRFLVGCHPSDGKCNLYADSAWENVKNV

IGPFMKAVCVEVEKTASCGVWDEWSPCSVTCGKGTRSRKREILHEGC

TSELQEQCEEERCLPKREPLDVPDEPEDDQPRPRGDNFAVEKPNENI

IDNNPQEPSPNPEEGKGENPNGFDLDENPENPPNPPNPPNPPNPPNP

PNPDIPEQEPNIPEDSEKEVPSDVPKNPEDDREENFDIPKKPENKHD

NQNNLPNDKSDRYIPYSPLSPKVLDNERKQSDPQSQDNNGNRHVPNS

EDRETRPHGRNNENRNYNRKHSNTPKHPEREEHEKPDNNKKKAGSDN

KYK⁵¹¹GTTSGTTRLLSGHTCFTLTGLLGTLVTMGLLT
```

The construct includes a signal peptide derived from murine IgG kappa V leader sequences as in the ET vectors. The TSR domain is underlined, and the VWA domain is indicated with dotted underlining. A FLAG tag sequence (which has been well characterized not to influence properties of proteins to which the tag is attached) is in bold followed by GSG linker, and the C55G mutation and N-linked site mutations are shown double underlined. The GPI anchor attachment signal from decay accelerating factor (DAF), which replaces the TRAP transmembrane and cytoplasmic domains, is shown in italics.

The construct was transfected into human 293T cells and immunofluorescent detection was used to detect expression of the FLAG tag. This TRAP ectodomain construct was highly expressed on cell surface.

Example 4

Conformation-Stabilizing TRAP Disulfide Mutations

The following experiments were done to create TRAP disulfide mutants that are locked in either the open or closed conformation. Mutation sites were selected based on the structures of *P. falciparum* as shown in FIG. 7.

TRAP without its repeat region (res. 26-288) was cloned into the ET5 vector N-terminal to the human IgG1 Fc fragment. The crystal structures of TRAP provide evidence of two distinct conformations, namely open and closed. Pairs of cysteine mutants were designed in PfTRAP in order to stabilize the construct in its open and closed conformations by a covalent disulfide bond. Cysteine mutations were introduced by Quickchange mutagenesis (Agilent technologies) and include the following pairs for further testing: K224C with Q78C, M231C with Q78C, A216C with N222C, N213C with A233C, and A216C with F230C.

HEK293S GnT-/- cells in 6-well dishes were transfected with mock, wtTRAP-Fc, five single mutant controls (Q78C, N231C, N222C, A216C, N213C), five double mutants (K224C+Q78C, M231C+Q78C, A216C+N222C, N213C+A233C, and A216C+F230C), and a western positive control (GARP-Fc) using Lipofectamine 2000 following the manufacturer's protocol (Invitrogen).

After 2 days, the supernatants were collected. Expressed Fc-tagged protein was immunoprecipitated using protein G beads (GE Healthcare). The beads and supernatant were incubated at room temperature, washed in TBS-T three times and once in PBS and final beads were resuspended in 1×SDS loading buffer. Samples were incubated at 95° C. for 5 minutes before loading on a 10% SDS-PAGE gel.

Samples were then transferred to a PVDF membrane using a Bio-rad Trans-Blot semi-dry transfer cell. The membrane was blocked in 5% Dry milk-TBST for 2 hours at room temperature and probed with anti-human IgG-HRP conjugate (1:1000 dilution) for 1 hour at room temperature. Signal was detected with ECL detection reagents (GE Healthcare).

As seen in FIG. 8, the double cysteine mutants A216C+N222C and A216C+F230C express close to wild type levels and represent the open and closed TRAP conformations respectively. These were later transfected into HEK293S GnT-/- cells, expanded to thirty 15 cm plates and 450 mL of supernatants were collected after five days.

As shown in FIG. 8, some mutants expressed better than others, which had little to no expression. For example, the K224C+Q78C open conformation mutant and N213C+A233C closed conformation mutants were not detectable on the gel, but the A216C+N222C open conformation mutant and the A216C+F230C closed conformation mutant showed robust expression. Some of the single mutants had good to excellent expression levels (Q78C, A216C), while other single mutants showed little to no detectable expression (N231C, N222C, N213C).

Example 5

Vaccination with TRAP Mutants

The following experiments are done to determine the antibody titre produced after vaccination of mice with the TRAP mutants described herein, and to determine persistence of immunity in immunized mice after challenge with sporozoite infection.

All mouse experiments use Balb/cJ females (The Jackson Laboratory) at 5-6 weeks initial age; *Anopheles stevensi* mosquitoes are used for all insect-mediated infections. A recombinant form of *Plasmodium berghei* expressing GFP (Franke-Fayard et al., Mol. Biochem. Parasitol. 137 23-33 (2004)) is used for in vivo infections.

Mice are immunized with mutant TRAP constructs as follows. Groups of mice receive IP injections of the constructs described herein, in a series of three injections total, at 2-week intervals. Each injection is with 10-100 micrograms of purified protein in saline with adjuvant, 200 microliters total volume. One group receives each injection with protein in Freund's adjuvant (injection #1 complete Freund's, injections #2 and #3 in incomplete Freund's), and a duplicate group for each construct receives each injection with alum as adjuvant. Proteins may be pre-treated with endoglycosidase H (endoH).

Antisera is harvested for in vitro tests as follows. Titer is checked at one week and two weeks following third-round injections for immunization by tail nick and harvest of 50-100 microliters of blood per animal, and prior to infection for animals tested for persistence of immunity as described below. The persistence of high antibody titers to the various antigens described above is tested by sampling sera once per month. For terminal blood harvest, animals are euthanized by isoflurane anaesthesia and secondarily by thoracotomy and cardiac puncture.

To maintain a pool of infected mosquitoes for mouse infections, a group of mice are injected intraperitoneally (IP) with *P. berghei*-infected red blood cells from a frozen stock. Beginning 5 days post-injection, mice are assayed for infection by tail nick and blood smear. At 5-8 days post-injection, mice that have reached the expected titer of 3-7% infection of red blood cells will be used for feeding mosquitoes. For feeding, mice are anaesthetized with ketamine-xylazine and draped on a mesh covering a box of naïve mosquitoes for 15 minutes. Post-feeding, mice are euthanized. At 22 or more days post-feeding, infection in mosquitoes reaches the sporozoite stage; select mosquitoes are assayed for infectious load by examination of salivary glands. The infection cycle is maintained by using some of these infected mosquitoes to bite and infect another group of naïve mice.

Injection of immunized mice with *P. berghei* sporozoites/infection assays are performed as follows Immunized mice as described above are infected by intravenous injection (via tail vein) of *P. berghei* sporozoites as described above. 20,000 sporozoites in a volume of 200 microliters sterile saline are used for each mouse, following established parameters for sporozoite-based infection (Mauduit et al., Inf. Imm. 78 2182-2188 (2010)). Beginning 5 days post injection, animals are monitored every two days for development of infection by tail nick and blood smear; infection in controls is expected to develop between 5 and 8 days post injection. Upon detection of infection, animals are monitored by blood smear daily. Upon reaching 7% infection of red blood cells, animals are sacrificed by $CO_2$ euthanasia; all animals will be sacrificed by 21 days post injection.

Challenge of immunized mice by mosquito-borne infection/infection assay is performed as follows. Separate cohorts of mice immunized as described above are subjected to mosquito-borne infection as described above. Mice are anaesthetized with ketamine (100 mg/kg)/xylazine (10 mg/kg) and exposed to infected mosquitoes for 15-minute feeding. For this procedure, mice are allowed to recover and are monitored by tail nick and blood smear at two-day intervals beginning on day 5 post-feeding. Controls in this series are expected to develop infection between 8 and 10 days post feeding Animals with detected infection are monitored daily by blood smear; animals reaching the threshold of 7% infected red blood cells will be euthanized. Animals in this series are euthanized by 21 days post feeding.

Persistence of immunity is tested at four weeks, three months, and one year following immunization, against infection via injected sporozoites and mosquito bite. Separate cohorts of mice in each immunization group described above have infection by either sporozoite injection or exposure to infected mosquitoes, with monitoring and euthanasia exactly as described above, beginning at 4 weeks, 3 months, and one year following their final immunization.

Example 6

Immunization of Mice with *P. falciparum*-based TRAP Constructs and Harvest of Antisera for In Vitro Infection Assays with Human Liver Cells A separate set of cohorts of mice will receive immunizations with constructs paralleling the series described in Example 5, but with proteins based on the TRAP sequence of the human pathogen *P. falciparum*. Titers will be determined as described above, and all animals in this series will have blood harvested following the last titer determination, as described above, for in vitro analyses of infection of human liver cells, e.g., as described in Hollingdale et al., J. Immunol., 132(2):909-913 (1984); Sattabongkot et al., Am J Trop Med Hyg, 74(5):708-715 (2006); Brahimi et al., Infect Immun 2001 June; 69(6):3845-52; Meis et al., Cell Biol Int Rep. 1985 November; 9(11):976. Alternatively or in addition, immunity is analysed in an animal model, e.g., in mice with chimeric human livers. See, e.g., Sacci et al., International Journal for Parasitology 36:353-360 (2006); Vaughan et al., Clin Invest. 122(10):3618-3628 (2012).

Example 7

Screening and Production of Monoclonal Antibody Against TRAP

Separate mice were immunized with TRAPF and TRAP6 with three injections (i.p. with complete Freund's adjuvant) on day 1, day 14, and day 28. Tail bleed was done on day 38 and elisa assays were performed to determine response. Titers were significant up to and including a dilution of 1:25000, as described in Example 2 earlier.

Myeloma cells were passaged the day before cell hybridization so that they were confluent the next day. Spleens from mice were isolated into a 60 mm dish with 10 mL of DMEM media+heparin. The spleens were teased apart to release splenocytes. Myeloma cells were washed once in 50 mL of DMEM then resuspended in 10 mL DMEM and counted. Spleen and myeloma cells were mixed at a 4:1 ratio. The cells were washed once in 50 mL DMEM then the media was aspirated and the pellet was gently suspended by flicking. The tube was placed in 37° C. water bath and 1 mL 50% w/w PEG was gradually added over 30 seconds, while stirring the pellet with a sterile pipet tip. After PEG was added, the mixture was left to stand at 37° C. for 1.5 minutes with occasional stirring. Over the next 3 minutes, 5 mL of 37° C. DMEM was gradually added with stirring. Then 14 mL of 37° C. DMEM was added over 1 minute. 30 mL of DMEM with 20% FBS was added and the mixture was centrifuged. The pellet was resuspended to $1.5 \times 10^6$ cell/mL, based on the number of spleen cells used. 5% Hybridoma Cloning Factor (PAA Laboratories S05-HCF) was added to stimulate growth. The final mixture was aliquoted at 0.2 mL/well in 96 well plates and incubated at 37° C. with 10% $CO_2$.

Cells were fed when the media turned from red to yellow 4 days after hybridization and every 2-3 days thereafter. To feed, about half of the media was removed by aspiration and replaced drop-wise using a 25 mL pipet. Cells were fed with DMEM 20% FBS+HAT (hypoxanthine aminopterin thymidine) media with L-gluatmine, gentamicin, pyruvate, 20%

FBS. After two weeks, cells were fed with DMEM 20% FBS+HT (hypoxanthine thymidine). After 30 days total, cells were fed with DMEM 20% FBS.

Wells containing successfully fused hybridoma cells were identified by ELISA. ELISA was done by coating the ELISA plate surface with Donkey anti-human IgG and incubated with TRAP-Fc supernatants. Hybridoma supernatants were screened for anti-TRAP antibody production on these plates, probed with Sheep anti-mouse antibody conjugated to HRP and detected with ABTS reagent (Invitrogen). Positive wells were expanded to T25 and single-cell cloned by limiting dilution into 96-well plates. Again, positive wells were identified by ELISA and expanded to T25 then diluted to 1, 3, and 30 cell/well in 3, 96-well plates. Positive clones were identified by ELISA. The final clones isolated were: CL1/5.1.1, CL1/8.2.3, CL2/1.4.3, and CL2/4.2.1 (see Table 4).

TABLE 4

| Clones | Screen | | | | P. vivax TRAP |
|---|---|---|---|---|---|
| | FL | Short | Open | Closed | |
| CL1/5.1.1 | 3.90 | 0.01 | 0 | 0 | — |
| CL1/8.2.3 | 3.50 | 0.02 | 0 | 0 | — |

TABLE 4-continued

| Clones | Screen | | | | P. vivax TRAP |
|---|---|---|---|---|---|
| | FL | Short | Open | Closed | |
| CL2/1.4.3 | — | 1.71 | 0.97 | 1.24 | — |
| CL2/4.2.1 | — | 0 | 0 | 0 | 0.83 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 24

<210> SEQ ID NO 1
<211> LENGTH: 274
<212> TYPE: PRT
<213> ORGANISM: Artificial Sequence
<220> FEATURE:
<223> OTHER INFORMATION: TRAP-6 fusion protein

<400> SEQUENCE: 1

Arg Asp Val Gln Asn Asn Ile Val Asp Glu Ile Lys Tyr Arg Glu Glu
1               5                   10                  15

Val Cys Asn Asp Glu Val Asp Leu Tyr Leu Leu Met Asp Gly Ser Gly
                20                  25                  30

Ser Ile Arg Arg His Asn Trp Val Asn His Ala Val Pro Leu Ala Met
            35                  40                  45

Lys Leu Ile Gln Gln Leu Asn Leu Asn Asp Asn Ala Ile His Leu Tyr
    50                  55                  60

Ala Ser Val Phe Ser Asn Asn Ala Arg Glu Ile Ile Arg Leu His Ser
65                  70                  75                  80

Asp Ala Ser Lys Asn Lys Glu Lys Ala Leu Ile Ile Ile Lys Ser Leu
                85                  90                  95

Leu Ser Thr Asn Leu Pro Tyr Gly Lys Thr Ser Leu Thr Asp Ala Leu
                100                 105                 110

Leu Gln Val Arg Lys His Leu Asn Asp Arg Ile Asn Arg Glu Asn Ala
            115                 120                 125

Asn Gln Leu Val Val Ile Leu Thr Asp Gly Ile Pro Asp Ser Ile Gln
        130                 135                 140

Asp Ser Leu Lys Glu Ser Arg Lys Leu Ser Asp Arg Gly Val Lys Ile
145                 150                 155                 160

Ala Val Phe Gly Ile Gly Gln Gly Ile Asn Val Ala Phe Asn Arg Phe
                165                 170                 175

Leu Val Gly Cys His Pro Ser Asp Gly Lys Cys Asn Leu Tyr Ala Asp
                180                 185                 190

Ser Ala Trp Glu Asn Val Lys Asn Val Ile Gly Pro Phe Met Lys Ala
```

```
            195                 200                 205
Val Cys Val Glu Val Lys Thr Ala Ser Cys Gly Val Trp Asp Glu
    210                 215                 220

Trp Ser Pro Cys Ser Val Thr Cys Gly Lys Gly Thr Arg Ser Arg Lys
225                 230                 235                 240

Arg Glu Ile Leu His Glu Gly Cys Thr Ser Glu Leu Gln Glu Gln Cys
                245                 250                 255

Glu Glu Glu Arg Cys Leu Pro Lys Arg Glu Pro Leu Asp Val Pro Asp
            260                 265                 270

Glu Pro

<210> SEQ ID NO 2
<211> LENGTH: 486
<212> TYPE: PRT
<213> ORGANISM: Artificial Sequence
<220> FEATURE:
<223> OTHER INFORMATION: TrapF

<400> SEQUENCE: 2

Arg Asp Val Gln Asn Asn Ile Val Asp Glu Ile Lys Tyr Arg Glu Glu
1               5                   10                  15

Val Cys Asn Asp Glu Val Asp Leu Tyr Leu Met Asp Gly Ser Gly Ser
                20                  25                  30

Ser Ile Arg Arg His Asn Trp Val Asn His Ala Val Pro Leu Ala Met
            35                  40                  45

Lys Leu Ile Gln Gln Leu Asn Leu Asn Asp Asn Ala Ile His Leu Tyr
        50                  55                  60

Ala Ser Val Phe Ser Asn Asn Ala Arg Glu Ile Ile Arg Leu His Ser
65                  70                  75                  80

Asp Ala Ser Lys Asn Lys Glu Lys Ala Leu Ile Ile Lys Ser Leu
                85                  90                  95

Leu Ser Thr Asn Leu Pro Tyr Gly Lys Thr Ser Leu Thr Asp Ala Leu
                100                 105                 110

Leu Gln Val Arg Lys His Leu Asn Asp Arg Ile Asn Arg Glu Asn Ala
            115                 120                 125

Asn Gln Leu Val Val Ile Leu Thr Asp Gly Ile Pro Asp Ser Ile Gln
        130                 135                 140

Asp Ser Leu Lys Glu Ser Arg Lys Leu Ser Asp Arg Gly Val Lys Ile
145                 150                 155                 160

Ala Val Phe Gly Ile Gly Gln Gly Ile Asn Val Ala Phe Asn Arg Phe
                165                 170                 175

Leu Val Gly Cys His Pro Ser Asp Gly Lys Cys Asn Leu Tyr Ala Asp
            180                 185                 190

Ser Ala Trp Glu Asn Val Lys Asn Val Ile Gly Pro Phe Met Lys Ala
        195                 200                 205

Val Cys Val Glu Val Lys Thr Ala Ser Cys Gly Val Trp Asp Glu
            210                 215                 220

Trp Ser Pro Cys Ser Val Thr Cys Gly Lys Gly Thr Arg Ser Arg Lys
225                 230                 235                 240

Arg Glu Ile Leu His Glu Gly Cys Thr Ser Glu Leu Gln Glu Gln Cys
                245                 250                 255

Glu Glu Glu Arg Cys Leu Pro Lys Arg Glu Pro Leu Asp Val Pro Asp
            260                 265                 270

Glu Pro Glu Asp Asp Gln Pro Arg Pro Arg Gly Asp Asn Phe Ala Val
        275                 280                 285
```

```
Glu Lys Pro Asn Glu Asn Ile Ile Asp Asn Asn Pro Gln Glu Pro Ser
            290                 295                 300

Pro Asn Pro Glu Glu Gly Lys Gly Glu Asn Pro Asn Gly Phe Asp Leu
305                 310                 315                 320

Asp Glu Asn Pro Glu Asn Pro Pro Asn Pro Asn Pro Pro Asn Pro Asn
                325                 330                 335

Pro Asn Pro Pro Asn Pro Pro Asn Pro Asp Ile Pro Glu Gln Glu Pro
            340                 345                 350

Asn Ile Pro Glu Asp Ser Glu Lys Glu Val Pro Ser Asp Val Pro Lys
            355                 360                 365

Asn Pro Glu Asp Asp Arg Glu Glu Asn Phe Asp Ile Pro Lys Lys Pro
370                 375                 380

Glu Asn Lys His Asp Asn Gln Asn Asn Leu Pro Asn Asp Lys Ser Asp
385                 390                 395                 400

Arg Tyr Ile Pro Tyr Ser Pro Leu Ser Pro Lys Val Leu Asp Asn Glu
                405                 410                 415

Arg Lys Gln Ser Asp Pro Gln Ser Gln Asp Asn Asn Gly Asn Arg His
            420                 425                 430

Val Pro Asn Ser Glu Asp Arg Glu Thr Arg Pro His Gly Arg Asn Asn
            435                 440                 445

Glu Asn Arg Asn Tyr Asn Arg Lys His Ser Asn Thr Pro Lys His Pro
450                 455                 460

Glu Arg Glu Glu His Glu Lys Pro Asp Asn Asn Lys Lys Lys Ala Gly
465                 470                 475                 480

Ser Asp Asn Lys Tyr Lys
                485

<210> SEQ ID NO 3
<211> LENGTH: 8
<212> TYPE: PRT
<213> ORGANISM: Artificial Sequence
<220> FEATURE:
<223> OTHER INFORMATION: 6-his tag

<400> SEQUENCE: 3

Ala His His His His His His Ala
1               5

<210> SEQ ID NO 4
<211> LENGTH: 552
<212> TYPE: PRT
<213> ORGANISM: Artificial Sequence
<220> FEATURE:
<223> OTHER INFORMATION: Flag-TRAP-GPI fusion protein

<400> SEQUENCE: 4

Met Asp Met Arg Val Pro Ala Gln Leu Leu Gly Leu Leu Leu Leu Trp
1               5                   10                  15

Phe Pro Gly Ser Arg Ser Leu Asp Tyr Lys Asp Asp Asp Lys Gly
                20                  25                  30

Ser Gly Arg Asp Val Gln Asn Asn Ile Val Asp Glu Ile Lys Tyr Arg
            35                  40                  45

Glu Glu Val Cys Asn Asp Glu Val Asp Leu Tyr Leu Leu Met Asp Gly
        50                  55                  60

Ser Gly Ser Ile Arg Arg His Asn Trp Val Asn His Ala Val Pro Leu
65                  70                  75                  80

Ala Met Lys Leu Ile Gln Gln Leu Asn Leu Asn Asp Asn Ala Ile His
```

```
                        85                  90                  95
Leu Tyr Ala Ser Val Phe Ser Asn Asn Ala Arg Glu Ile Ile Arg Leu
            100                 105                 110

His Ser Asp Ala Ser Lys Asn Lys Glu Lys Ala Leu Ile Ile Ile Lys
            115                 120                 125

Ser Leu Leu Ser Thr Asn Leu Pro Tyr Gly Lys Thr Ser Leu Thr Asp
    130                 135                 140

Ala Leu Leu Gln Val Arg Lys His Leu Asn Asp Arg Ile Asn Arg Glu
145                 150                 155                 160

Asn Ala Asn Gln Leu Val Val Ile Leu Thr Asp Gly Ile Pro Asp Ser
            165                 170                 175

Ile Gln Asp Ser Leu Lys Glu Ser Arg Lys Leu Ser Asp Arg Gly Val
            180                 185                 190

Lys Ile Ala Val Phe Gly Ile Gly Gln Gly Ile Asn Val Ala Phe Asn
            195                 200                 205

Arg Phe Leu Val Gly Cys His Pro Ser Asp Gly Lys Cys Asn Leu Tyr
    210                 215                 220

Ala Asp Ser Ala Trp Glu Asn Val Lys Asn Val Ile Gly Pro Phe Met
225                 230                 235                 240

Lys Ala Val Cys Val Glu Val Glu Lys Thr Ala Ser Cys Gly Val Trp
            245                 250                 255

Asp Glu Trp Ser Pro Cys Ser Val Thr Cys Gly Lys Gly Thr Arg Ser
            260                 265                 270

Arg Lys Arg Glu Ile Leu His Glu Gly Cys Thr Ser Glu Leu Gln Glu
    275                 280                 285

Gln Cys Glu Glu Glu Arg Cys Leu Pro Lys Arg Glu Pro Leu Asp Val
    290                 295                 300

Pro Asp Glu Pro Glu Asp Asp Gln Pro Arg Pro Arg Gly Asp Asn Phe
305                 310                 315                 320

Ala Val Glu Lys Pro Asn Glu Asn Ile Ile Asp Asn Asn Pro Gln Glu
            325                 330                 335

Pro Ser Pro Asn Pro Glu Glu Gly Lys Gly Glu Asn Pro Asn Gly Phe
            340                 345                 350

Asp Leu Asp Glu Asn Pro Glu Asn Pro Pro Asn Pro Pro Asn Pro Pro
    355                 360                 365

Asn Pro Pro Asn Pro Pro Asn Pro Pro Asn Pro Asp Ile Pro Glu Gln
    370                 375                 380

Glu Pro Asn Ile Pro Glu Asp Ser Gly Lys Glu Val Pro Ser Asp Val
385                 390                 395                 400

Pro Lys Asn Pro Glu Asp Asp Arg Glu Glu Asn Phe Asp Ile Pro Lys
            405                 410                 415

Lys Pro Glu Asn Lys His Asp Asn Asn Asn Leu Pro Asn Asp Lys
            420                 425                 430

Ser Asp Arg Tyr Ile Pro Tyr Ser Pro Leu Ser Pro Lys Val Leu Asp
    435                 440                 445

Asn Glu Arg Lys Gln Ser Asp Pro Gln Ser Gln Asp Asn Asn Gly Asn
    450                 455                 460

Arg His Val Pro Asn Ser Glu Asp Arg Glu Thr Arg Pro His Gly Arg
465                 470                 475                 480

Asn Asn Glu Asn Arg Asn Tyr Asn Arg Lys His Ser Asn Thr Pro Lys
            485                 490                 495

His Pro Glu Arg Glu Glu His Glu Lys Pro Asp Asn Asn Lys Lys Lys
            500                 505                 510
```

-continued

```
Ala Gly Ser Asp Asn Lys Tyr Lys Gly Thr Thr Ser Gly Thr Thr Arg
        515                 520                 525

Leu Leu Ser Gly His Thr Cys Phe Thr Leu Thr Gly Leu Leu Gly Thr
530                 535                 540

Leu Val Thr Met Gly Leu Leu Thr
545                 550

<210> SEQ ID NO 5
<211> LENGTH: 574
<212> TYPE: PRT
<213> ORGANISM: Plasmodium falciparum

<400> SEQUENCE: 5

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Arg Glu Val Cys Asn Asp Glu Val Asp
        35                  40                  45

Leu Tyr Leu Leu Met Asp Cys Ser Gly Ser Ile Arg Arg His Asn Trp
50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Ala Ser Val Phe Ser Asn Asn
                85                  90                  95

Ala Arg Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
        115                 120                 125

Gly Lys Thr Asn Leu Thr Asp Ala Leu Leu Gln Val Arg Lys His Leu
130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Ser Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Glu Arg Cys Leu Pro
        275                 280                 285

Lys Arg Glu Pro Leu Asp Val Pro Asp Glu Pro Glu Asp Asp Gln Pro
        290                 295                 300

Arg Pro Arg Gly Asp Asn Phe Ala Val Glu Lys Pro Asn Glu Asn Ile
305                 310                 315                 320

Ile Asp Asn Asn Pro Gln Glu Pro Ser Pro Asn Pro Glu Glu Gly Lys
```

```
                    325                 330                 335
Gly Glu Asn Pro Asn Gly Phe Asp Leu Asp Glu Asn Pro Glu Asn Pro
                340                 345                 350

Pro Asn Pro Pro Asn Pro Pro Asn Pro Pro Asn Pro Pro Asn Pro Pro
            355                 360                 365

Asn Pro Asp Ile Pro Glu Gln Glu Pro Asn Ile Pro Glu Asp Ser Glu
        370                 375                 380

Lys Glu Val Pro Ser Asp Val Pro Lys Asn Pro Glu Asp Asp Arg Glu
385                 390                 395                 400

Glu Asn Phe Asp Ile Pro Lys Lys Pro Glu Asn Lys His Asp Asn Gln
                405                 410                 415

Asn Asn Leu Pro Asn Asp Lys Ser Asp Arg Tyr Ile Pro Tyr Ser Pro
            420                 425                 430

Leu Ser Pro Lys Val Leu Asp Asn Glu Arg Lys Gln Ser Asp Pro Gln
        435                 440                 445

Ser Gln Asp Asn Asn Gly Asn Arg His Val Pro Asn Ser Glu Asp Arg
    450                 455                 460

Glu Thr Arg Pro His Gly Arg Asn Asn Glu Asn Arg Ser Tyr Asn Arg
465                 470                 475                 480

Lys His Asn Asn Thr Pro Lys His Pro Glu Arg Glu His Glu Lys
                485                 490                 495

Pro Asp Asn Lys Lys Lys Ala Gly Ser Asp Asn Lys Tyr Lys Ile
            500                 505                 510

Ala Gly Gly Ile Ala Gly Gly Leu Ala Leu Leu Ala Cys Ala Gly Leu
        515                 520                 525

Ala Tyr Lys Phe Val Val Pro Gly Ala Ala Thr Pro Tyr Ala Gly Glu
    530                 535                 540

Pro Ala Pro Phe Asp Glu Thr Leu Gly Glu Glu Asp Lys Asp Leu Asp
545                 550                 555                 560

Glu Pro Glu Gln Phe Arg Leu Pro Glu Glu Asn Glu Trp Asn
                565                 570
```

<210> SEQ ID NO 6
<211> LENGTH: 556
<212> TYPE: PRT
<213> ORGANISM: Plasmodium vivax

<400> SEQUENCE: 6

```
Met Lys Leu Leu Gln Asn Lys Ser Tyr Leu Val Val Phe Leu Leu
1               5                   10                  15

Tyr Val Ser Ile Phe Ala Arg Gly Asp Glu Lys Val Val Asp Glu Val
                20                  25                  30

Lys Tyr Ser Glu Glu Val Cys Asn Glu Ser Val Asp Leu Tyr Leu Leu
            35                  40                  45

Val Asp Gly Ser Gly Ser Ile Gly Tyr Pro Asn Trp Ile Thr Lys Val
        50                  55                  60

Ile Pro Met Leu Asn Gly Leu Ile Asn Ser Leu Ser Leu Ser Arg Asp
65                  70                  75                  80

Thr Ile Asn Leu Tyr Met Asn Leu Phe Gly Asn Tyr Thr Thr Glu Leu
                85                  90                  95

Ile Arg Leu Gly Ser Gly Gln Ser Ile Asp Lys Arg Gln Ala Leu Ser
            100                 105                 110

Lys Val Thr Glu Leu Arg Lys Thr Tyr Thr Pro Tyr Gly Thr Thr Asn
        115                 120                 125
```

```
Met Thr Ala Ala Leu Asp Glu Val Gln Lys His Leu Asn Asp Arg Val
        130                 135                 140

Asn Arg Glu Lys Ala Ile Gln Leu Val Ile Leu Met Thr Asp Gly Val
145                 150                 155                 160

Pro Asn Ser Lys Tyr Arg Ala Leu Glu Val Ala Asn Lys Leu Lys Gln
                165                 170                 175

Arg Asn Val Ser Leu Ala Val Ile Gly Val Gly Gln Gly Ile Asn His
                180                 185                 190

Gln Phe Asn Arg Leu Ile Ala Gly Cys Arg Pro Arg Glu Pro Asn Cys
            195                 200                 205

Lys Phe Tyr Ser Tyr Ala Asp Trp Asn Glu Ala Val Ala Leu Ile Lys
            210                 215                 220

Pro Phe Ile Ala Lys Val Cys Thr Glu Val Glu Arg Val Ala Asn Cys
225                 230                 235                 240

Gly Pro Trp Asp Pro Trp Thr Ala Cys Ser Val Thr Cys Gly Arg Gly
                245                 250                 255

Thr His Ser Arg Ser Arg Pro Ser Leu His Glu Lys Cys Thr Thr His
                260                 265                 270

Met Val Ser Glu Cys Glu Glu Gly Cys Pro Val Glu Pro Glu Pro
            275                 280                 285

Leu Pro Val Pro Ala Pro Leu Pro Thr Val Pro Glu Asp Val Asn Pro
290                 295                 300

Arg Asp Thr Asp Asp Glu Asn Glu Asn Pro Asn Phe Asn Lys Gly Leu
305                 310                 315                 320

Asp Val Pro Asp Glu Asp Asp Glu Val Pro Pro Ala Asn Glu Gly
                325                 330                 335

Ala Asp Gly Asn Pro Val Glu Glu Asn Val Phe Pro Pro Ala Asp Asp
                340                 345                 350

Ser Val Pro Asp Glu Ser Asn Val Leu Pro Leu Pro Ala Val Pro
            355                 360                 365

Gly Gly Ser Ser Glu Glu Phe Pro Ala Asp Val Gln Asn Asn Pro Asp
370                 375                 380

Ser Pro Glu Glu Leu Pro Met Glu Gln Glu Val Pro Gln Asp Asn Asn
385                 390                 395                 400

Val Asn Glu Pro Glu Arg Ser Asp Ser Asn Gly Tyr Gly Val Asn Glu
                405                 410                 415

Lys Val Ile Pro Asn Pro Leu Asp Asn Glu Arg Asp Met Ala Asn Lys
                420                 425                 430

Asn Lys Thr Val His Pro Gly Arg Lys Asp Ser Ala Arg Asp Arg Tyr
            435                 440                 445

Ala Arg Pro His Gly Ser Thr His Val Asn Asn Arg Ala Asn Glu
450                 455                 460

Asn Ser Asp Ile Pro Asn Asn Pro Val Pro Ser Asp Tyr Glu Gln Pro
465                 470                 475                 480

Glu Asp Lys Ala Lys Ser Ser Asn Asn Gly Tyr Lys Ile Ala Gly
                485                 490                 495

Gly Val Ile Ala Gly Leu Ala Leu Val Gly Cys Val Gly Phe Ala Tyr
                500                 505                 510

Asn Phe Val Ala Gly Gly Ala Ala Gly Met Ala Gly Glu Pro Ala
            515                 520                 525

Pro Phe Asp Glu Ala Met Ala Glu Asp Glu Lys Asp Val Ala Glu Ala
530                 535                 540

Asp Gln Phe Lys Leu Pro Glu Asp Asn Asp Trp Asn
```

545                 550                 555

<210> SEQ ID NO 7
<211> LENGTH: 579
<212> TYPE: PRT
<213> ORGANISM: Plasmodium knowlesi

<400> SEQUENCE: 7

Met Lys Leu Leu Gln Asn Lys Ser Tyr Leu Val Val Phe Leu Leu
1               5                   10                  15

Tyr Val Ser Ile Phe Ala Arg Gly Asp Gln Lys Ile Val Asp Val
                20                  25                  30

Lys Tyr Asn Glu Glu Val Cys Asn Glu Lys Val Asp Leu Tyr Leu Leu
                35                  40                  45

Val Asp Gly Ser Gly Ser Ile Gly Tyr Ala Asn Trp Ile Thr Arg Val
        50                  55                  60

Ile Pro Met Leu Thr Gly Leu Ile Glu Asn Leu Asn Leu Ser Lys Asp
65              70                  75                  80

Ser Ile Asn Leu Tyr Met Ser Leu Phe Ala Ser His Thr Thr Glu Leu
                85                  90                  95

Ile Arg Leu Gly Ser Gly Pro Ser Met Asp Lys Lys Gln Ala Leu Asn
                100                 105                 110

Val Val Arg Asp Leu Arg Lys Gly Tyr Glu Pro Tyr Gly Asn Thr Ser
            115                 120                 125

Met Ser Ser Ala Leu Ser Glu Val Glu Met His Leu Lys Asp Arg Val
130             135                 140

Asn Arg Pro Asn Ala Ile Gln Leu Val Ile Leu Met Thr Asp Gly Ile
145             150                 155                 160

Pro Asn Asn Lys Tyr Arg Ala Leu Glu Leu Ser Arg Ala Leu Lys Glu
                165                 170                 175

Arg Asn Val Lys Leu Ala Val Ile Gly Ile Gly Gln Gly Ile Asn His
            180                 185                 190

Gln Tyr Asn Lys Leu Met Ala Gly Cys Arg Pro Arg Glu Arg Ser Cys
        195                 200                 205

Lys Phe Tyr Ser Ser Ala Asp Trp Ser Glu Ala Ile Ser Leu Ile Lys
210             215                 220

Pro Phe Ile Ala Lys Val Cys Thr Glu Val Glu Arg Ile Ala Lys Cys
225             230                 235                 240

Gly Pro Trp Asp Asp Trp Thr Pro Cys Ser Val Thr Cys Gly Lys Gly
                245                 250                 255

Thr His Ser Arg Ser Arg Pro Leu Leu His Ala Gly Cys Thr Thr His
            260                 265                 270

Met Val Lys Glu Cys Glu Met Asp Glu Cys Pro Val Glu Pro Glu Pro
        275                 280                 285

Val Pro Val Pro Ala Pro Val Pro Pro Thr Pro Glu Asp Glu Asn Pro
        290                 295                 300

Arg Thr Thr Asp Glu Glu Asp Asp His Pro Asn Phe His Gln Gly Leu
305             310                 315                 320

Asp Val Pro Asp Val Glu Asn Asp Val Pro Pro Glu Asn Asp Gly Gly
                325                 330                 335

Asp Gly Asn Pro Phe Glu Glu Asn Phe Phe Pro Pro Gly Asp Asp Thr
            340                 345                 350

Val Pro Asp Glu Ser Asn Val Ile Pro Val Pro Pro Thr Val Pro Gly
        355                 360                 365

Gly Ser Asn Ser Glu Phe Ser Ser Asp Val Glu Asn Ala Ala Gln Tyr
370                 375                 380

Pro Glu Asn Pro Glu Asn Pro Glu Asn Pro Glu Asn Ser Glu Asn Pro
385                 390                 395                 400

Glu Asn Pro Glu Asn Gln Asn Asn Pro Glu Asp Phe Pro Met Glu Pro
            405                 410                 415

Asp Met Ser Ala Asp Asn Lys Ile Asn Glu Pro Thr Asn Pro Ser Asp
            420                 425                 430

Ser Gly Gln Gly Ile Pro Glu Asn Val Ile Pro Thr Pro Ile Asn Asn
            435                 440                 445

Glu Lys Asp Ile Ile Asn Lys Asn Lys Ala Val Tyr Pro Asn Gly Ser
450                 455                 460

Asn Gln Ser His Asp Arg Tyr Pro Lys Pro His Arg Asn Ala Gly Gly
465                 470                 475                 480

Tyr Asp Asn Asn Pro Asn Ala Asn Ser Asp Ile Pro Glu Gly Pro Phe
            485                 490                 495

Ser Ser Glu Glu Glu Gln Pro Gly Asp Lys Gly Lys Lys Ser Ser Asn
            500                 505                 510

Asn Gly Tyr Lys Ile Ala Gly Gly Val Ile Ala Gly Leu Ala Leu Val
            515                 520                 525

Gly Cys Val Gly Phe Ala Tyr Asn Phe Val Ser Ser Gly Gly Ala Ala
            530                 535                 540

Gly Met Ala Gly Glu Pro Ala Pro Phe Asp Glu Ala Met Ala Glu Asp
545                 550                 555                 560

Glu Lys Asp Ala Gly Glu Ala Asp Gln Phe Lys Leu Pro Glu Asp Asn
            565                 570                 575

Asp Trp Asn

<210> SEQ ID NO 8
<211> LENGTH: 476
<212> TYPE: PRT
<213> ORGANISM: Plasmodium chabaudi

<400> SEQUENCE: 8

Cys Lys Leu Phe Ile Asp Val Asp Lys Leu Phe Thr Lys Gly Ser Val
1               5                   10                  15

Asn Glu Thr Leu Phe Asn Asp Ser Tyr Lys Asn Phe Cys Pro Lys Gly
            20                  25                  30

Gly Cys Asn Thr Asn Tyr Asp Arg Ile Gly Ala Leu Cys Glu Tyr Leu
            35                  40                  45

Leu Glu Glu Leu Ser Lys Asn Asp Lys Gln Lys Gly Asp Asn Asn
50                  55                  60

Asn Val Asn Gln Asn Tyr Glu Tyr Val Phe Met Trp Leu Ala Ala Lys
65                  70                  75                  80

Phe Leu Asn Ile Thr His Asp Val Ser Phe Ser Leu Asn Asp Tyr Tyr
            85                  90                  95

Glu Lys Phe Ile Val Asn Gln Gly Gly His Phe Asn Cys Trp Gly Lys
            100                 105                 110

Leu Asp Asn Lys Glu Tyr Leu Lys Asp Ser Asn Leu Ser Ile Met Ser
            115                 120                 125

Val Phe Tyr Gln Leu Phe Met Asn Ile Cys Lys Ala Val Val Glu Asn
            130                 135                 140

Glu Ile Ser Lys Leu Glu Thr Lys Phe Met Met Ile Asp Tyr Asn
145                 150                 155                 160

```
Tyr Tyr Gln Ile Tyr Asp Leu Ile Asn Ser Gln Phe Ser Ser Cys Asp
            165                 170                 175

Pro Tyr Val Gln Leu Leu Ile Asn Leu Lys Lys Leu Tyr Asp Glu Tyr
        180                 185                 190

Arg Asn Leu Ala Ile Lys Gln Ile Pro Lys Asp Gln His Asp Thr Val
        195                 200                 205

Asn Ser Leu Thr Cys Pro Glu Ile Asn Asn Asn Asp Asn Gln Pro Asn
        210                 215                 220

Leu Gln Phe Gln Ser Asn Gly Cys Lys Glu Leu His Asp Phe Phe Arg
225                 230                 235                 240

Gln Ile Ser Arg Lys Arg Lys Pro Lys Arg Pro Ser Lys Gly Ser Lys
            245                 250                 255

Ser Ser Ser Asn Tyr Ser Lys Thr Lys Asn Glu Thr Lys Ser Asn
            260                 265                 270

Lys Gly Glu Leu Lys Lys Thr Thr Ser Asp Ala Glu Lys Asn Glu Arg
        275                 280                 285

Ser Gln Lys Asn Thr Asp Gln Ser Thr Ile Lys Glu Asn Pro Pro Ser
        290                 295                 300

Glu Pro Lys Val Pro Glu Ser Lys Ala Pro Asp Ile Pro Gln Asn Gly
305                 310                 315                 320

Asn Ala Gln Thr Gln Thr Ser Ser Lys Ser Pro Glu Lys Ile Gln Glu
            325                 330                 335

Gly Ser Pro Asn His Asn Pro Val Ser Ser Asp Ala Lys Asp Thr Pro
            340                 345                 350

Lys Asp Met Gly Ser Ile Ser Glu Asn Ser Val Asn Gln Ser Thr Thr
        355                 360                 365

Pro Lys Asn Ile Ser Lys Gly Asp Ile Ser Leu Ser Lys Lys Pro Gln
        370                 375                 380

Ala Gln Gln Gln Asn Val Pro Leu Pro Gln Phe Pro Glu Pro Ile Asp
385                 390                 395                 400

Lys Lys Ile Gln Leu Lys Pro Glu Asn Lys Ala Val Asp Ser Asn Asp
            405                 410                 415

Lys Phe Pro Gly Thr Gly Ile Asn Gln Glu Lys Ser Ile Lys Gln Glu
            420                 425                 430

Asn Leu Pro Asn Ser Thr Ser Gln His Gln Glu Glu Asn Pro Lys Thr
        435                 440                 445

Lys Asn Thr Asp Leu His Gln Pro Asn Gln Gln Ile Cys Lys Asn Gln
        450                 455                 460

Trp Met Lys Thr Lys Asn Leu Gln Ile Leu Tyr His
465                 470                 475

<210> SEQ ID NO 9
<211> LENGTH: 545
<212> TYPE: PRT
<213> ORGANISM: Plasmodium cynomolgi

<400> SEQUENCE: 9

Glu Ile Lys Tyr Ser Glu Glu Val Cys Asn Glu Ser Val Asp Leu Tyr
1               5                   10                  15

Leu Leu Ile Asp Gly Ser Gly Ser Ile Gly Tyr Pro Asn Trp Ile Thr
            20                  25                  30

Arg Val Ile Pro Met Leu Ser Gly Leu Ile Gly Asn Leu Ser Leu Ser
        35                  40                  45

Arg Asp Ala Ile Asn Leu Tyr Met Ser Leu Phe Ala Asn His Thr Thr
    50                  55                  60
```

```
Glu Leu Ile Arg Leu Gly Ser Gly Pro Ser Val Asp Lys Lys Leu Ala
 65                  70                  75                  80

Leu Asp Ser Ser Ser Glu Leu Arg Lys Thr Tyr Val Pro Tyr Gly Ala
                 85                  90                  95

Thr Asn Met Ser Ser Ala Leu Ala Glu Val Glu Met His Leu Lys Asp
            100                 105                 110

Arg Val Asn Arg Glu Lys Ala Ile Gln Leu Val Ile Leu Leu Thr Asp
            115                 120                 125

Gly Val Pro Asn Asn Lys Phe Arg Val Val Glu Leu Ser Lys Ala Leu
130                 135                 140

Lys Glu Lys Asn Val Lys Leu Ala Val Ile Gly Ile Gly His Gly Ile
145                 150                 155                 160

Asn His His Phe Asn Arg Leu Ile Ala Gly Cys Ser Pro Arg Gln Glu
                165                 170                 175

Asn Cys Lys Phe Tyr Ser Tyr Ala Glu Trp Asn Glu Ala Val Ala Leu
            180                 185                 190

Ile Lys Pro Phe Ile Ala Lys Val Cys Thr Glu Val Glu Lys Val Ala
            195                 200                 205

Asn Cys Gly Pro Trp Asn Pro Trp Thr Pro Cys Ser Val Thr Cys Gly
210                 215                 220

Lys Gly Thr His Ser Arg Ser Arg Pro Leu Val His Glu Gly Cys Thr
225                 230                 235                 240

Thr His Met Val Asn Glu Cys Glu Glu Gln Glu Cys Pro Val Glu Pro
                245                 250                 255

Glu Pro Val Pro Val Pro Ala Pro Phe Pro Thr Val Pro Glu Asp Leu
            260                 265                 270

Lys Pro Arg Asn Thr Asp Asp Asp Asp Asp His Pro Asn Phe His
            275                 280                 285

Lys Glu Leu Asp Val Pro Asp Val Glu Asp Val Pro Pro Glu Asn
            290                 295                 300

Asp Val Asp Gly Asn Pro Ala Glu Glu Ser Asp Phe Pro Pro Thr Asp
305                 310                 315                 320

Asp Ala Val Pro Glu Glu Ser Asn Val Leu Pro Val Pro Pro Val Val
                325                 330                 335

Pro Gly Gly Ser Thr Asp Glu Phe Pro Thr Asp Val Arg Asn Ser Pro
            340                 345                 350

Met Asn Pro Glu Asn Pro Glu Asn Ser Glu Tyr Pro Glu Asn Pro Glu
            355                 360                 365

Ser Pro Glu Asn Pro Asn Asn Pro Glu Glu Ser Pro Met Glu Gln Glu
            370                 375                 380

Val Pro Gln Asp Asn Asn Ile Asn Glu Pro Glu Arg Ser Asp Gly Lys
385                 390                 395                 400

Val Asn Gly Ile Asn His Lys Leu Ile Pro Lys Pro Met Asp Asn Glu
                405                 410                 415

Lys Asp Ile Asn Lys Asn Lys Lys Val His Pro Ser Ser Ser Asn His
            420                 425                 430

Ala His Asp Arg Tyr Ala Arg Pro His Arg Ser Ser Gly Gly Asn Asp
            435                 440                 445

Asn Gly Arg Ile Ala Asn Ser Asp Leu Pro Arg Ala Pro Val Ala Ser
            450                 455                 460

Asp Tyr Glu Gln Pro Glu Asp Lys Gly Lys Lys Ser Ser Asn Asn Gly
465                 470                 475                 480
```

-continued

```
Tyr Lys Ile Ala Gly Val Ile Ala Gly Leu Ala Leu Val Gly Cys
            485                 490                 495

Val Gly Phe Ala Tyr Leu Phe Val Ala Ser Gly Gly Ala Ala Gly Met
        500                 505                 510

Ala Gly Glu Pro Ala Pro Phe Asp Glu Ala Met Ala Glu Asp Asp Lys
        515                 520                 525

Asp Thr Ala Glu Ala Asp Gln Phe Lys Leu Pro Glu Asp Asn Asp Trp
        530                 535                 540

Asn
545

<210> SEQ ID NO 10
<211> LENGTH: 827
<212> TYPE: PRT
<213> ORGANISM: Plasmodium yoelii

<400> SEQUENCE: 10

Met Lys Leu Leu Gly Asn Ser Lys Tyr Ile Phe Val Val Leu Leu Leu
1               5                   10                  15

Cys Ile Ser Val Phe Leu Asn Gly Gln Glu Thr Leu Asp Glu Ile Lys
            20                  25                  30

Tyr Ser Glu Glu Val Cys Thr Glu Gln Ile Asp Ile His Ile Leu Leu
        35                  40                  45

Asp Gly Ser Gly Ser Ile Gly Tyr Ser Asn Trp Lys Ala His Val Ile
    50                  55                  60

Pro Met Leu Asn Thr Leu Val Asp Asn Leu Asn Ile Ser Asn Asp Glu
65                  70                  75                  80

Ile Asn Val Ser Leu Thr Leu Phe Ser Thr Asn Ser Arg Glu Leu Ile
                85                  90                  95

Lys Leu Lys Gly Tyr Gly Ser Thr Ser Lys Asp Ser Leu Arg Phe Ile
            100                 105                 110

Leu Ala His Leu Gln Asn Asn Tyr Ser Pro Asn Gly Asn Thr Asn Leu
        115                 120                 125

Thr Ser Ala Leu Leu Val Val Asp Thr Leu Ile Asn Glu Arg Met Tyr
    130                 135                 140

Arg Pro Asp Ala Ile Gln Leu Ala Ile Ile Leu Thr Asp Gly Ile Pro
145                 150                 155                 160

Asn Asp Leu Pro Arg Ser Thr Ala Val Val His Gln Leu Lys Arg Lys
                165                 170                 175

His Val Asn Val Ala Ile Ile Gly Val Gly Ala Gly Val Asn Asn Glu
            180                 185                 190

Tyr Asn Arg Ile Leu Val Gly Cys Asp Arg Tyr Ala Pro Cys Pro Tyr
        195                 200                 205

Tyr Ser Ser Gly Ser Trp Asn Glu Ala Gln Asn Met Ile Lys Pro Phe
    210                 215                 220

Leu Thr Lys Val Cys Gln Glu Val Glu Arg Ile Ala His Cys Gly Lys
225                 230                 235                 240

Trp Glu Glu Trp Ser Glu Cys Ser Thr Thr Cys Asp Glu Gly Arg Lys
                245                 250                 255

Ile Arg Arg Arg Gln Ile Leu His Pro Gly Cys Val Ser Glu Met Thr
            260                 265                 270

Thr Pro Cys Lys Val Arg Asp Cys Pro Gln Ile Pro Ile Pro Pro Val
        275                 280                 285

Ile Pro Asn Lys Ile Pro Glu Lys Pro Ser Asn Pro Glu Glu Pro Val
    290                 295                 300
```

```
Asn Pro Asn Asp Pro Asn Asp Pro Asn Asn Pro Asn Asn Pro Asn Asn
305                 310                 315                 320

Pro Asn Asn Pro Asn Asn Pro Asn Asn Pro Asn Asn Pro Asn Asn Pro
            325                 330                 335

Asn Asn Pro Asn Asn Pro Asn Asn Pro Asn Asn Pro Asn Asn Pro Asn
        340                 345                 350

Asn Pro Asn Asn Pro Asn Asn Pro Asn Asn Pro Asn Asn Pro Asn Asn
    355                 360                 365

Pro Asn Asn Pro Asn Asn Pro Asn Asn Pro Asn Asn Pro Asn Asp Pro
370                 375                 380

Ser Asn Pro Asn Asn Pro Asn Pro Lys Lys Arg Asn Pro Lys Arg Arg
385                 390                 395                 400

Asn Pro Asn Lys Pro Lys Pro Asn Lys Pro Asn Pro Asn Lys Pro Asn
            405                 410                 415

Pro Asn Glu Pro Ser Asn Pro Asn Lys Pro Asn Pro Asn Glu Pro Ser
        420                 425                 430

Asn Pro Asn Lys Pro Asn Pro Asn Glu Pro Ser Asn Pro Asn Lys Pro
    435                 440                 445

Asn Pro Asn Glu Pro Ser Asn Pro Asn Lys Pro Asn Pro Asn Glu Pro
450                 455                 460

Leu Asn Pro Asn Glu Pro Ser Asn Pro Asn Glu Pro Ser Asn Pro Asn
465                 470                 475                 480

Ala Pro Ser Asn Pro Asn Glu Pro Ser Asn Pro Asn Glu Pro Ser Asn
            485                 490                 495

Pro Asn Glu Pro Ser Asn Pro Asn Glu Pro Ser Asn Pro Asn Glu Pro
        500                 505                 510

Ser Asn Pro Lys Lys Pro Ser Asn Pro Asn Glu Pro Ser Asn Pro Asn
    515                 520                 525

Glu Pro Leu Asn Pro Asn Glu Pro Ser Asn Pro Asn Glu Pro Ser Asn
530                 535                 540

Pro Asn Glu Pro Ser Asn Pro Glu Glu Pro Ser Asn Pro Lys Glu Pro
545                 550                 555                 560

Ser Asn Pro Asn Glu Pro Ser Asn Pro Glu Glu Pro Asn Pro Glu Glu
            565                 570                 575

Pro Ser Asn Pro Lys Glu Pro Ser Asn Pro Glu Glu Pro Ile Asn Pro
        580                 585                 590

Glu Glu Leu Asn Pro Lys Glu Pro Ser Asn Pro Glu Glu Ser Asn Pro
    595                 600                 605

Lys Glu Pro Ile Asn Pro Glu Glu Ser Asn Pro Lys Glu Pro Ile Asn
610                 615                 620

Pro Glu Asp Asn Glu Asn Pro Leu Ile Ile Gln Asp Glu Pro Ile Glu
625                 630                 635                 640

Pro Arg Asn Asp Ser Asn Val Ile Pro Ile Leu Pro Ile Ile Pro Gln
            645                 650                 655

Lys Gly Asn Asn Ile Pro Ser Asn Leu Pro Glu Asn Pro Ser Asp Ser
        660                 665                 670

Glu Val Glu Tyr Pro Arg Pro Asn Asp Asn Gly Glu Asn Ser Asn Asn
    675                 680                 685

Thr Met Lys Ser Lys Lys Asn Ile Pro Asn Glu Pro Ile Pro Ser Pro
690                 695                 700

Gly Asp Asn Pro Tyr Lys Gly His Glu Glu Arg Ile Pro Lys Pro His
705                 710                 715                 720
```

```
Arg Ser Asn Asp Asp Tyr Val Tyr Asp Asn Asn Val Asn Lys Asn Asn
                725                 730                 735

Lys Asp Glu Pro Glu Ile Pro Asn Asn Glu Tyr Glu Glu Asp Lys Asn
            740                 745                 750

Lys Asn Gln Ser Lys Ser Asn Asn Gly Tyr Lys Ile Ala Gly Gly Ile
        755                 760                 765

Ile Gly Gly Leu Ala Ile Leu Gly Cys Ala Gly Val Gly Tyr Asn Phe
    770                 775                 780

Ile Ala Gly Ser Ser Ala Ala Gly Leu Ala Ala Glu Pro Ala Pro
785                 790                 795                 800

Phe Glu Asp Val Ile Pro Asp Asp Lys Asp Ile Val Glu Asn Glu
                805                 810                 815

Gln Phe Lys Leu Pro Glu Asp Asn Asp Trp Asn
            820                 825

<210> SEQ ID NO 11
<211> LENGTH: 421
<212> TYPE: PRT
<213> ORGANISM: Plasmodium berghei

<400> SEQUENCE: 11

Met Lys Leu Leu Gly Asn Ser Lys Tyr Phe Val Val Leu Leu Leu
1               5                   10                  15

Cys Ile Ser Val Phe Leu Asn Gly Gln Glu Ile Leu Asp Glu Ile Lys
            20                  25                  30

Tyr Ser Glu Glu Val Cys Asn Glu Gln Ile Asp Leu His Ile Leu Leu
        35                  40                  45

Asp Gly Ser Gly Ser Ile Gly His Ser Asn Trp Ile Ser His Val Ile
    50                  55                  60

Pro Met Leu Thr Thr Leu Val Asp Asn Leu Asn Ile Ser Arg Asp Glu
65                  70                  75                  80

Ile Asn Ile Ser Met Thr Leu Phe Ser Thr Tyr Ala Arg Glu Leu Val
                85                  90                  95

Arg Leu Lys Arg Tyr Gly Ser Thr Ser Lys Ala Ser Leu Arg Phe Ile
            100                 105                 110

Ile Ala Gln Leu Gln Asn Asn Tyr Ser Pro His Gly Thr Thr Asn Leu
        115                 120                 125

Thr Ser Ala Leu Leu Asn Val Asp Asn Leu Ile Gln Lys Lys Met Asn
    130                 135                 140

Arg Pro Asn Ala Ile Gln Leu Val Ile Leu Thr Asp Gly Ile Pro
145                 150                 155                 160

Asn Asn Leu Lys Lys Ser Thr Thr Val Val Asn Gln Leu Lys Lys Lys
                165                 170                 175

Asp Val Asn Val Ala Ile Ile Gly Val Gly Ala Gly Val Asn Asn Met
            180                 185                 190

Phe Asn Arg Ile Leu Val Gly Cys Gly Lys Leu Gly Pro Cys Pro Tyr
        195                 200                 205

Tyr Ser Tyr Gly Ser Trp Asp Gln Ala Gln Thr Met Ile Lys Pro Phe
    210                 215                 220

Leu Ser Lys Val Cys Gln Glu Val Glu Lys Val Ala Leu Cys Gly Lys
225                 230                 235                 240

Trp Glu Glu Trp Ser Glu Cys Ser Thr Thr Cys Asp Asn Gly Thr Lys
                245                 250                 255

Ile Arg Lys Arg Lys Val Leu His Pro Asn Cys Ala Gly Glu Met Thr
            260                 265                 270
```

```
Ala Pro Cys Lys Val Arg Asp Cys Pro Pro Lys Pro Val Ala Pro Pro
            275                 280                 285

Val Ile Pro Ile Lys Val Pro Asp Val Pro Val Lys Pro Val Glu Pro
        290                 295                 300

Ile Glu Pro Ala Glu Pro Ala Glu Pro Ala Glu Pro Ala Glu Pro Ala
305                 310                 315                 320

Glu Pro Ala Glu Pro Ala Glu Pro Ala Glu Pro Ala Glu Pro Ala Glu
            325                 330                 335

Pro Ala Glu Pro Ala Glu Pro Ala Glu Pro Ala Glu Pro Ala Glu Pro
            340                 345                 350

Ala Glu Pro Ala Glu Pro Ala Glu Pro Ala Glu Pro Ala Lys Pro Ala
            355                 360                 365

Glu Pro Ala Glu Pro Ala Glu Pro Ala Glu Pro Ala Glu Pro Val Asn
        370                 375                 380

Pro Asp Asn Pro Ile Leu Pro Ile Lys Pro Glu Glu Pro Ser Gly Gly
385                 390                 395                 400

Ala Glu Pro Leu Asn Pro Val Glu Asn Pro Phe Ile Ile Pro Asp
            405                 410                 415

Glu Pro Ile Glu Pro
            420

<210> SEQ ID NO 12
<211> LENGTH: 614
<212> TYPE: PRT
<213> ORGANISM: Plasmodium gallinaceu

<400> SEQUENCE: 12

Met Lys Ile Phe Leu Ser Asn Lys Phe Leu Leu Phe Ile Phe Phe Leu
1               5                   10                  15

Tyr Phe Ser Thr Val Val Lys Gly Ala Asp Gln Ile Val Asp Glu Ile
            20                  25                  30

Thr Tyr Asn Glu Gln Ile Cys His Glu Lys Val Asp Leu Tyr Leu Leu
        35                  40                  45

Met Asp Gly Ser Gly Ser Ile Gly Tyr Tyr Asn Trp Val Thr Tyr Ala
    50                  55                  60

Val Pro Leu Val Glu Glu Ile Val Gln Asn Leu Asn Ile Ser Lys Gln
65                  70                  75                  80

Gly Ile His Leu Tyr Leu Ser Val Phe Thr His Ile Leu Lys Glu Tyr
                85                  90                  95

Ile Pro Leu Asn Ser Ile Phe Ser Thr Asn Arg Asp Phe Ala Leu Asn
            100                 105                 110

Val Ile Arg Ser Leu Arg Thr Lys Tyr Ser Gln Asn Gly Ser Thr Asn
        115                 120                 125

Leu Thr Leu Ala Leu Ser Arg Val Leu Lys Asn Tyr Phe Leu Thr Lys
    130                 135                 140

Gly Ser Arg Glu Asp Ala Val Gln Leu Val Ile Phe Thr Asp Gly
145                 150                 155                 160

Ser Pro Asp Asn Lys Glu Ser Ala Met Lys Glu Val Asn Lys Leu Lys
                165                 170                 175

Lys Met Lys Ala Lys Phe Ala Val Ile Gly Val Gly Met Gly Ile Asn
            180                 185                 190

Lys Glu Phe Asn Lys Ser Leu Val Gly Cys Pro Leu Lys Glu Lys Lys
        195                 200                 205

Cys Asp Leu Tyr Ser Glu Ala Ser Trp Asn Glu Val Gln Asn Val Ile
```

```
                    210                 215                 220
Ala Pro Phe Leu Lys Glu Val Cys Ile Glu Val Glu Lys Val Ala His
225                 230                 235                 240

Cys Gly Ser Trp Gly Glu Trp Ser Pro Cys Ser Val Thr Cys Gly Glu
                245                 250                 255

Gly Val Arg Thr Arg Arg Arg Glu Val Leu His Lys Gly Cys Thr Asp
                260                 265                 270

His Met Thr Val Leu Cys Glu Lys Pro Asn Cys Pro Glu Ile Val Lys
            275                 280                 285

Pro Asn Ile Thr Asp Val Pro Asp Val Pro Asp Glu Glu Pro Glu Pro
        290                 295                 300

Ile Pro Glu Glu Lys Lys Pro Glu Pro Val Pro Glu Glu Lys Lys Pro
305                 310                 315                 320

Glu Ser Ala Pro Glu Glu Lys Asn Pro Glu Ser Val Pro Glu Glu Lys
                325                 330                 335

Lys Pro Glu Ser Val Pro Glu Glu Lys Glu Pro Glu Ser Val Pro Glu
            340                 345                 350

Glu Lys Glu Pro Glu Ser Val Pro Glu Glu Lys Glu Pro Glu Ser Ala
        355                 360                 365

Pro Glu Glu Lys Lys Pro Glu Ser Asp Pro Glu Glu Lys Lys Leu Glu
    370                 375                 380

Pro Ile Pro Glu Gly Lys Lys Ile Glu Pro Ile Pro Glu Glu Glu Lys
385                 390                 395                 400

Leu Glu Pro Ile Pro Glu Glu Lys Pro Glu Ser Val Thr Glu Asp
                405                 410                 415

Arg Glu Ser Glu Pro Val Pro Asp Gly Glu Ala Glu Asn Val Pro Gln
            420                 425                 430

Asn Ile Pro Asp Asp Glu Gln Glu Lys Ile Ser Gly Asp Ile Pro
        435                 440                 445

Asn Asp Glu Glu Leu Ile Pro Lys Asn Glu Pro Asp Asp Ile Lys Arg
    450                 455                 460

Asn Glu Tyr Asp Thr Thr Pro Asn Ile Ile Pro Pro Lys Asp Thr Tyr
465                 470                 475                 480

Asn Asp Asn Glu Ile Thr Asn Pro Ile Ser Glu Glu Asp Asn Glu Asn
                485                 490                 495

Lys Thr Lys Val Glu Asp Arg Val Pro Arg Pro His Asn Thr Asp Ser
            500                 505                 510

Glu Tyr Ile Pro Pro Lys Arg Asp Asn His Lys Asp Glu Pro Ser Arg
        515                 520                 525

Arg Lys Arg Glu Asn Glu Gly Thr Gln Gly Lys Thr Lys Lys Thr Ser
    530                 535                 540

Leu Asn Asp Asn Lys Tyr Lys Ile Ala Gly Ile Ile Gly Gly Leu
545                 550                 555                 560

Ala Leu Leu Gly Cys Ala Gly Phe Ala Tyr Lys Phe Leu Thr Gln Thr
                565                 570                 575

Pro Thr Pro Pro Ile Thr Ser Glu Ala Ala Pro Phe Asp Asp Val Leu
            580                 585                 590

Ala Glu Gly Glu Lys Asp Ile Glu Glu Asn Glu Gln Phe Lys Leu Pro
        595                 600                 605

Glu Asp Asn Asp Trp Asn
    610

<210> SEQ ID NO 13
```

-continued

```
<211> LENGTH: 570
<212> TYPE: PRT
<213> ORGANISM: Plasmodium relictum

<400> SEQUENCE: 13

His Glu Lys Val Asp Leu Tyr Ile Leu Met Asp Gly Ser Gly Ser Ile
1               5                   10                  15

Gly Tyr Asp Asn Trp Ile Ser Tyr Ala Val Pro Leu Val Tyr Asp Ile
            20                  25                  30

Val Lys Asn Leu Asn Val Ser Asn Asp Gly Ile His Leu Tyr Leu Ser
        35                  40                  45

Val Phe Thr His Tyr Leu Arg Glu Tyr Ile Lys Leu Gly Ser Ser Leu
    50                  55                  60

Ser Thr Asn Arg Glu Phe Ala Leu Asn Ile Ile Glu Asn Leu Lys Asn
65                  70                  75                  80

Lys Tyr Tyr Leu His Gly Ser Thr Asn Leu Thr Ile Ala Leu Ser Arg
                85                  90                  95

Val Leu Gln Asp Asn Phe Ile Lys Lys Gly Arg Glu Asp Ala Val
            100                 105                 110

Gln Leu Ile Leu Ile Phe Thr Asp Gly Ala Pro Asp Asp Lys Glu Thr
        115                 120                 125

Ala Met Gln Glu Val Val Lys Leu Lys Lys Met Asn Ala Lys Phe Ser
    130                 135                 140

Val Ile Gly Val Gly Met Gly Ile Asn Arg Glu Phe Asn Lys Arg Leu
145                 150                 155                 160

Val Asp Cys Ser Pro Tyr Glu Glu Lys Cys Asp Leu Tyr Ser Glu Ala
                165                 170                 175

Ser Trp Val Asp Val Lys Asp Ile Ile Ala Pro Phe Leu Lys Lys Val
            180                 185                 190

Cys Val Glu Ile Glu Lys Val Ala His Cys Gly Ser Trp Gly Glu Trp
        195                 200                 205

Thr Pro Cys Ser Val Thr Cys Gly Glu Gly Ile Lys Thr Arg Lys Arg
    210                 215                 220

Asn Ile Leu His Lys Gly Cys Ser Asp His Met Asn Ala Leu Cys Glu
225                 230                 235                 240

Lys Pro Glu Cys Pro Ala Ile Ile Lys Pro Ser Val Thr Asp Ile Pro
                245                 250                 255

Lys Val Ile Pro Glu Asp Asn Arg Arg Gly Asp Val Pro Asp Asn Val
            260                 265                 270

Pro Glu Asn Lys Lys Arg Gly Asp Val Pro Asp Tyr Phe Pro Glu Asp
        275                 280                 285

Asn Lys Pro Leu Val Pro Asp Asn Val Pro Asn Asn Asp Pro Asp Asn
    290                 295                 300

Ala Pro Glu Asn Lys Lys Arg Gly Asp Val Pro Asp Tyr Phe Pro Glu
305                 310                 315                 320

Asn Asn Gln Pro Glu Val Pro Asn Ala Pro Glu Asn Gln Pro
                325                 330                 335

Glu Val Pro Asp Asn Val Pro Glu Glu Asn Gln Pro Glu Val Pro Tyr
            340                 345                 350

Asn Val Pro Glu Glu Asn Gln Pro Glu Val Pro Asp Asn Val Pro Glu
        355                 360                 365

Glu Asn Gln Pro Glu Val Pro Asp Asn Val Pro Glu Asp Arg Asn Pro
    370                 375                 380

Glu Ile Pro Glu Glu Lys Lys Pro Glu Asn Ile Pro Glu Asn Arg Lys
```

```
                    385                 390                 395                 400

Glu Glu Ile Ile Glu Tyr Ile Pro Lys Asn Ile Pro Asp Asp Val Glu
                        405                 410                 415

Ile Leu Pro Asn Glu Asn Pro Arg Ile Ile Lys Asp Gln Arg His
                    420                 425                 430

Leu Pro Pro Gln Val Val Pro Ala Lys Asn Ile His Asn Glu Asn Gln
                        435                 440                 445

Ile Ile Asn Lys Val Pro Glu His Asn Gly Asn Ile Asn Lys Thr Thr
                    450                 455                 460

Val Glu Asp Arg Glu Leu Arg Pro His Asn Thr Asp Asn Glu Tyr Ile
        465                 470                 475                 480

Arg Pro Arg Asn Asp Tyr Lys Val Glu Pro Ser Thr Glu Asn Val
                        485                 490                 495

Glu Asn Glu Asn Ser Glu Glu Lys Asn Lys Ala Pro Ser Asp Asn
                    500                 505                 510

Lys Tyr Lys Ile Ala Gly Gly Ile Ile Gly Gly Leu Ala Leu Leu Gly
                    515                 520                 525

Cys Ala Gly Phe Ala Tyr Lys Phe Leu Ala His Ala Pro Thr Pro Pro
                    530                 535                 540

Met Thr Ser Glu Gly Ala Pro Phe Asn Asp Val Leu Gly Glu Gly Glu
        545                 550                 555                 560

Lys Asp Ile Glu Glu Asn Glu Gln Phe Lys
                        565                 570

<210> SEQ ID NO 14
<211> LENGTH: 8
<212> TYPE: PRT
<213> ORGANISM: Artificial Sequence
<220> FEATURE:
<223> OTHER INFORMATION: FLAG sequences

<400> SEQUENCE: 14

Asp Tyr Lys Asp Asp Asp Asp Lys
1               5

<210> SEQ ID NO 15
<211> LENGTH: 259
<212> TYPE: PRT
<213> ORGANISM: Plasmodium vivax

<400> SEQUENCE: 15

Asp Glu Lys Val Val Asp Glu Val Lys Tyr Ser Glu Glu Val Cys Asn
1               5                   10                  15

Glu Gln Val Asp Leu Tyr Leu Leu Val Asp Gly Ser Gly Ser Ile Gly
                    20                  25                  30

Tyr Pro Asn Trp Ile Thr Lys Val Ile Pro Met Leu Asn Gly Leu Ile
                35                  40                  45

Asn Ser Leu Ser Leu Ser Arg Asp Thr Ile Asn Leu Tyr Met Asn Leu
            50                  55                  60

Phe Gly Ser Tyr Thr Thr Glu Leu Ile Arg Leu Gly Ser Gly Gln Ser
65              70                  75                  80

Ile Asp Lys Arg Gln Ala Leu Ser Lys Val Thr Glu Leu Arg Lys Thr
                85                  90                  95

Tyr Thr Pro Tyr Gly Thr Thr Ser Met Thr Ala Ala Leu Asp Glu Val
                    100                 105                 110

Gln Lys His Leu Asn Asp Arg Val Asn Arg Glu Lys Ala Ile Gln Leu
                115                 120                 125
```

Val Ile Leu Met Thr Asp Gly Val Pro Asn Ser Lys Tyr Arg Ala Leu
            130                 135                 140

Glu Val Ala Asn Lys Leu Lys Gln Arg Asn Val Arg Leu Ala Val Ile
145                 150                 155                 160

Gly Ile Gly Gln Gly Ile Asn His Gln Phe Asn Arg Leu Ile Ala Gly
                165                 170                 175

Cys Arg Pro Arg Glu Pro Asn Cys Lys Phe Tyr Ser Tyr Ala Asp Trp
            180                 185                 190

Asn Glu Ala Val Ala Leu Ile Lys Pro Phe Ile Ala Lys Val Cys Thr
        195                 200                 205

Glu Val Glu Arg Val Ala Asn Cys Gly Pro Trp Asp Pro Trp Thr Ala
210                 215                 220

Cys Ser Val Thr Cys Gly Arg Gly Thr His Ser Arg Ser Arg Pro Ser
225                 230                 235                 240

Leu His Glu Lys Cys Thr Thr His Met Val Ser Glu Cys Glu Glu Gly
                245                 250                 255

Glu Cys Pro

<210> SEQ ID NO 16
<211> LENGTH: 912
<212> TYPE: DNA
<213> ORGANISM: Artificial Sequence
<220> FEATURE:
<223> OTHER INFORMATION: TRAP-6 protein

<400> SEQUENCE: 16
atggatatga gagttcctgc tcaattgctg gggttgctct tgctctggtt cagtggggtg      60
ttggggaggg atgtgcagaa taacattgtg gacgagatca gtaccgcga ggaggtatgc     120
aatgacgagg tggatttgta tctcttgatg gatggctccg gatcgatcag gaggcacaac     180
tgggtcaatc atgcggtccc cctggccatg aagctgatcc agcagctgaa tctcaacgac     240
aatgccattc acctctatgc cagcgtgttc tcaaacaacg cgagagagat catccgcttg     300
cacagcgacg cttcgaagaa caaggaaaag gcactcatca ttatcaaatc gttgctctca     360
acgaatcttc cgtacggtaa aacgtcattg accgacgcac tgttgcaagt ccgcaaacat     420
ctgaacgata gaatcaaccg cgagaatgcg aatcagcttg tagtaatcct gacggacggt     480
attcccgatt cgattcaaga ttcactcaag gaaagcagga actttcaga cagaggcgtg     540
aaaatcgctg tgtttggaat tggtcaggga atcaacgtgg cattcaacag gttcctggtc     600
ggttgtcacc cctccgatgg aaaatgcaat ctctacgcgg actcagcgtg gaaaacgtc      660
aagaacgtga tcggacccct tatgaaagcc gtctgtgtcg aggtagagaa accgcgtcg     720
tgtggagtgt gggatgagtg gtcaccgtgc tccgtcacgt gcggaaaagg aactaggagc     780
cgcaagaggg agatccttca cgaaggctgc acatcggagt tgcaagagca gtgtgaagaa     840
gagaggtgcc tcccgaagcg cgaacctctt gacgtaccgg atgaaccagc gcatcaccat     900
caccatcacg cg                                                           912

<210> SEQ ID NO 17
<211> LENGTH: 259
<212> TYPE: PRT
<213> ORGANISM: Artificial Sequence
<220> FEATURE:
<223> OTHER INFORMATION: fragment of plasmodium vivax TRAP

<400> SEQUENCE: 17

Asp Glu Lys Val Val Asp Glu Val Lys Tyr Ser Glu Glu Val Cys Asn
1               5                   10                  15

Glu Ser Val Asp Leu Tyr Leu Leu Val Asp Gly Ser Gly Ser Ile Gly
            20                  25                  30

Tyr Pro Asn Trp Ile Thr Lys Val Ile Pro Met Leu Asn Gly Leu Ile
        35                  40                  45

Asn Ser Leu Ser Leu Ser Arg Asp Thr Ile Asn Leu Tyr Met Asn Leu
    50                  55                  60

Phe Gly Asn Tyr Thr Thr Glu Leu Ile Arg Leu Gly Ser Gly Gln Ser
65                  70                  75                  80

Ile Asp Lys Arg Gln Ala Leu Ser Lys Val Thr Glu Leu Arg Lys Thr
                85                  90                  95

Tyr Thr Pro Tyr Gly Thr Thr Asn Met Thr Ala Ala Leu Asp Glu Val
            100                 105                 110

Gln Lys His Leu Asn Asp Arg Val Asn Arg Glu Lys Ala Ile Gln Leu
        115                 120                 125

Val Ile Leu Met Thr Asp Gly Val Pro Asn Ser Lys Tyr Arg Ala Leu
    130                 135                 140

Glu Val Ala Asn Lys Leu Lys Gln Arg Asn Val Ser Leu Ala Val Ile
145                 150                 155                 160

Gly Ile Gly Gln Gly Ile Asn His Gln Phe Asn Arg Leu Ile Ala Gly
                165                 170                 175

Cys Arg Pro Arg Glu Pro Asn Cys Lys Phe Tyr Ser Tyr Ala Asp Trp
            180                 185                 190

Asn Glu Ala Val Ala Leu Ile Lys Pro Phe Ile Ala Lys Val Cys Thr
        195                 200                 205

Glu Val Glu Arg Val Ala Asn Cys Gly Pro Trp Asp Pro Trp Thr Ala
    210                 215                 220

Cys Ser Val Thr Cys Gly Arg Gly Thr His Ser Arg Ser Arg Pro Ser
225                 230                 235                 240

Leu His Glu Lys Cys Thr Thr His Met Val Ser Glu Cys Glu Glu Gly
                245                 250                 255

Glu Cys Pro

<210> SEQ ID NO 18
<211> LENGTH: 262
<212> TYPE: PRT
<213> ORGANISM: Artificial Sequence
<220> FEATURE:
<223> OTHER INFORMATION: fragment of plasmodium falciparum TRAP

<400> SEQUENCE: 18

Arg Asp Val Gln Asn Asn Ile Val Asp Glu Ile Lys Tyr Arg Glu Glu
1               5                   10                  15

Val Cys Asn Asp Glu Val Asp Leu Tyr Leu Leu Met Asp Cys Ser Gly
            20                  25                  30

Ser Ile Arg Arg His Asn Trp Val Asn His Ala Val Pro Leu Ala Met
        35                  40                  45

Lys Leu Ile Gln Gln Leu Asn Leu Asn Asp Asn Ala Ile His Leu Tyr
    50                  55                  60

Ala Ser Val Phe Ser Asn Asn Ala Arg Glu Ile Ile Arg Leu His Ser
65                  70                  75                  80

Asp Ala Ser Lys Asn Lys Glu Lys Ala Leu Ile Ile Ile Lys Ser Leu
                85                  90                  95

Leu Ser Thr Asn Leu Pro Tyr Gly Lys Thr Asn Leu Thr Asp Ala Leu

```
            100                 105                 110
Leu Gln Val Arg Lys His Leu Asn Asp Arg Ile Asn Arg Glu Asn Ala
        115                 120                 125

Asn Gln Leu Val Val Ile Leu Thr Asp Gly Ile Pro Asp Ser Ile Gln
    130                 135                 140

Asp Ser Leu Lys Glu Ser Arg Lys Leu Ser Asp Arg Gly Val Lys Ile
145                 150                 155                 160

Ala Val Phe Gly Ile Gly Gln Gly Ile Asn Val Ala Phe Asn Arg Phe
                165                 170                 175

Leu Val Gly Cys His Pro Ser Asp Gly Lys Cys Asn Leu Tyr Ala Asp
            180                 185                 190

Ser Ala Trp Glu Asn Val Lys Asn Val Ile Gly Pro Phe Met Lys Ala
        195                 200                 205

Val Cys Val Glu Val Glu Lys Thr Ala Ser Cys Gly Val Trp Asp Glu
    210                 215                 220

Trp Ser Pro Cys Ser Val Thr Cys Gly Lys Gly Thr Arg Ser Arg Lys
225                 230                 235                 240

Arg Glu Ile Leu His Glu Gly Cys Thr Ser Glu Leu Gln Glu Gln Cys
                245                 250                 255

Glu Glu Glu Arg Cys Pro
            260

<210> SEQ ID NO 19
<211> LENGTH: 253
<212> TYPE: PRT
<213> ORGANISM: Artificial Sequence
<220> FEATURE:
<223> OTHER INFORMATION: dragment of plasmodium cynomulgi TRAP

<400> SEQUENCE: 19

Glu Ile Lys Tyr Ser Glu Glu Val Cys Asn Glu Ser Val Asp Leu Tyr
1               5                   10                  15

Leu Leu Ile Asp Gly Ser Gly Ser Ile Gly Tyr Pro Asn Trp Ile Thr
            20                  25                  30

Arg Val Ile Pro Met Leu Ser Gly Leu Ile Gly Asn Leu Ser Leu Ser
        35                  40                  45

Arg Asp Ala Ile Asn Leu Tyr Met Ser Leu Phe Ala Asn His Thr Thr
    50                  55                  60

Glu Leu Ile Arg Leu Gly Ser Gly Pro Ser Val Asp Lys Lys Leu Ala
65                  70                  75                  80

Leu Asp Ser Ser Ser Glu Leu Arg Lys Thr Tyr Val Pro Tyr Gly Ala
                85                  90                  95

Thr Asn Met Ser Ser Ala Leu Ala Glu Val Glu Met His Leu Lys Asp
            100                 105                 110

Arg Val Asn Arg Glu Lys Ala Ile Gln Leu Val Ile Leu Leu Thr Asp
        115                 120                 125

Gly Val Pro Asn Asn Lys Phe Arg Val Val Glu Leu Ser Lys Ala Leu
    130                 135                 140

Lys Glu Lys Asn Val Lys Leu Ala Val Ile Gly Ile Gly His Gly Ile
145                 150                 155                 160

Asn His His Phe Asn Arg Leu Ile Ala Gly Cys Ser Pro Arg Gln Glu
                165                 170                 175

Asn Cys Lys Phe Tyr Ser Tyr Ala Glu Trp Asn Glu Ala Val Ala Leu
            180                 185                 190

Ile Lys Pro Phe Ile Ala Lys Val Cys Thr Glu Val Glu Lys Val Ala
```

```
                 195                 200                 205
Asn Cys Gly Pro Trp Asn Pro Trp Thr Pro Cys Ser Val Thr Cys Gly
210                 215                 220

Lys Gly Thr His Ser Arg Ser Arg Pro Leu Val His Glu Gly Cys Thr
225                 230                 235                 240

Thr His Met Val Asn Glu Cys Glu Glu Gln Glu Cys Pro
                245                 250
```

<210> SEQ ID NO 20
<211> LENGTH: 259
<212> TYPE: PRT
<213> ORGANISM: Artificial Sequence
<220> FEATURE:
<223> OTHER INFORMATION: fragment of plasmodium knowlesi TRAP

<400> SEQUENCE: 20

```
Asp Gln Lys Ile Val Asp Glu Val Lys Tyr Asn Glu Val Cys Asn
1               5                   10                  15

Glu Lys Val Asp Leu Tyr Leu Val Asp Gly Ser Gly Ser Ile Gly
                20                  25                  30

Tyr Ala Asn Trp Ile Thr Arg Val Ile Pro Met Leu Thr Gly Leu Ile
                35                  40                  45

Glu Asn Leu Asn Leu Ser Lys Asp Ser Ile Asn Leu Tyr Met Ser Leu
50                  55                  60

Phe Ala Ser His Thr Thr Glu Leu Ile Arg Leu Gly Ser Gly Pro Ser
65                  70                  75                  80

Met Asp Lys Lys Gln Ala Leu Asn Val Val Arg Asp Leu Arg Lys Gly
                85                  90                  95

Tyr Glu Pro Tyr Gly Asn Thr Ser Met Ser Ser Ala Leu Ser Glu Val
                100                 105                 110

Glu Met His Leu Lys Asp Arg Val Asn Arg Pro Asn Ala Ile Gln Leu
                115                 120                 125

Val Ile Leu Met Thr Asp Gly Ile Pro Asn Asn Lys Tyr Arg Ala Leu
                130                 135                 140

Glu Leu Ser Arg Ala Leu Lys Glu Arg Asn Val Lys Leu Ala Val Ile
145                 150                 155                 160

Gly Ile Gly Gln Gly Ile Asn His Gln Tyr Asn Lys Leu Met Ala Gly
                165                 170                 175

Cys Arg Pro Arg Glu Arg Ser Cys Lys Phe Tyr Ser Ser Ala Asp Trp
                180                 185                 190

Ser Glu Ala Ile Ser Leu Ile Lys Pro Phe Ile Ala Lys Val Cys Thr
                195                 200                 205

Glu Val Glu Arg Ile Ala Lys Cys Gly Pro Trp Asp Asp Trp Thr Pro
                210                 215                 220

Cys Ser Val Thr Cys Gly Lys Gly Thr His Ser Arg Ser Arg Pro Leu
225                 230                 235                 240

Leu His Ala Gly Cys Thr Thr His Met Val Lys Glu Cys Glu Met Asp
                245                 250                 255

Glu Cys Pro
```

<210> SEQ ID NO 21
<211> LENGTH: 257
<212> TYPE: PRT
<213> ORGANISM: Artificial Sequence
<220> FEATURE:
<223> OTHER INFORMATION: fragment of plasmodium berghei TRAP

<400> SEQUENCE: 21

```
Gln Glu Ile Leu Asp Glu Ile Lys Tyr Ser Glu Glu Val Cys Asn Glu
1               5                   10                  15
Gln Ile Asp Leu His Ile Leu Asp Gly Ser Gly Ser Ile Gly His
            20                  25                  30
Ser Asn Trp Ile Ser His Val Ile Pro Met Leu Thr Thr Leu Val Asp
            35                  40                  45
Asn Leu Asn Ile Ser Arg Asp Glu Ile Asn Ile Ser Met Thr Leu Phe
        50                  55                  60
Ser Thr Tyr Ala Arg Glu Leu Val Arg Leu Lys Arg Tyr Gly Ser Thr
65                  70                  75                  80
Ser Lys Ala Ser Leu Arg Phe Ile Ile Ala Gln Leu Gln Asn Asn Tyr
                85                  90                  95
Ser Pro His Gly Thr Thr Asn Leu Thr Ser Ala Leu Leu Asn Val Asp
            100                 105                 110
Asn Leu Ile Gln Lys Lys Met Asn Arg Pro Asn Ala Ile Gln Leu Val
            115                 120                 125
Ile Ile Leu Thr Asp Gly Ile Pro Asn Asn Leu Lys Lys Ser Thr Thr
        130                 135                 140
Val Val Asn Gln Leu Lys Lys Asp Val Asn Val Ala Ile Ile Gly
145                 150                 155                 160
Val Gly Ala Gly Val Asn Asn Met Phe Asn Arg Ile Leu Val Gly Cys
                165                 170                 175
Gly Lys Leu Gly Pro Cys Pro Tyr Tyr Ser Tyr Gly Ser Trp Asp Gln
            180                 185                 190
Ala Gln Thr Met Ile Lys Pro Phe Leu Ser Lys Val Cys Gln Glu Val
            195                 200                 205
Glu Lys Val Ala Leu Cys Gly Lys Trp Glu Glu Trp Ser Glu Cys Ser
        210                 215                 220
Thr Thr Cys Asp Asn Gly Thr Lys Ile Arg Lys Arg Lys Val Leu His
225                 230                 235                 240
Pro Asn Cys Ala Gly Glu Met Thr Ala Pro Cys Lys Val Arg Asp Cys
                245                 250                 255
Pro
```

<210> SEQ ID NO 22
<211> LENGTH: 257
<212> TYPE: PRT
<213> ORGANISM: Artificial Sequence
<220> FEATURE:
<223> OTHER INFORMATION: fragment of plasmodium yoelii TRAP

<400> SEQUENCE: 22

```
Gln Glu Thr Leu Asp Glu Ile Lys Tyr Ser Glu Glu Val Cys Thr Glu
1               5                   10                  15
Gln Ile Asp Ile His Ile Leu Asp Gly Ser Gly Ser Ile Gly Tyr
            20                  25                  30
Ser Asn Trp Lys Ala His Val Ile Pro Met Leu Asn Thr Leu Val Asp
            35                  40                  45
Asn Leu Asn Ile Ser Asn Asp Glu Ile Asn Val Ser Leu Thr Leu Phe
        50                  55                  60
Ser Thr Asn Ser Arg Glu Leu Ile Lys Leu Lys Gly Tyr Gly Ser Thr
65                  70                  75                  80
Ser Lys Asp Ser Leu Arg Phe Ile Leu Ala His Leu Gln Asn Asn Tyr
                85                  90                  95
```

```
Ser Pro Asn Gly Asn Thr Asn Leu Thr Ser Ala Leu Leu Val Val Asp
            100                 105                 110

Thr Leu Ile Asn Glu Arg Met Tyr Arg Pro Asp Ala Ile Gln Leu Ala
        115                 120                 125

Ile Ile Leu Thr Asp Gly Ile Pro Asn Asp Leu Pro Arg Ser Thr Ala
    130                 135                 140

Val Val His Gln Leu Lys Arg Lys His Val Asn Val Ala Ile Ile Gly
145                 150                 155                 160

Val Gly Ala Gly Val Asn Asn Glu Tyr Asn Arg Ile Leu Val Gly Cys
                165                 170                 175

Asp Arg Tyr Ala Pro Cys Pro Tyr Tyr Ser Ser Gly Ser Trp Asn Glu
            180                 185                 190

Ala Gln Asn Met Ile Lys Pro Phe Leu Thr Lys Val Cys Gln Glu Val
        195                 200                 205

Glu Arg Ile Ala His Cys Gly Lys Trp Glu Glu Trp Ser Glu Cys Ser
    210                 215                 220

Thr Thr Cys Asp Glu Gly Arg Lys Ile Arg Arg Arg Gln Ile Leu His
225                 230                 235                 240

Pro Gly Cys Val Ser Glu Met Thr Thr Pro Cys Lys Val Arg Asp Cys
                245                 250                 255

Pro

<210> SEQ ID NO 23
<211> LENGTH: 260
<212> TYPE: PRT
<213> ORGANISM: Artificial Sequence
<220> FEATURE:
<223> OTHER INFORMATION: fragment of plasmodium gallinaceum TRAP

<400> SEQUENCE: 23

Ala Asp Gln Ile Val Asp Glu Ile Thr Tyr Asn Glu Gln Ile Cys His
1               5                   10                  15

Glu Lys Val Asp Leu Tyr Leu Leu Met Asp Gly Ser Gly Ser Ile Gly
            20                  25                  30

Tyr Tyr Asn Trp Val Thr Tyr Ala Val Pro Leu Val Glu Glu Ile Val
        35                  40                  45

Gln Asn Leu Asn Ile Ser Lys Gln Gly Ile His Leu Tyr Leu Ser Val
    50                  55                  60

Phe Thr His Ile Leu Lys Glu Tyr Ile Pro Leu Asn Ser Ile Phe Ser
65                  70                  75                  80

Thr Asn Arg Asp Phe Ala Leu Asn Val Ile Arg Ser Leu Arg Thr Lys
                85                  90                  95

Tyr Ser Gln Asn Gly Ser Thr Asn Leu Thr Leu Ala Leu Ser Arg Val
            100                 105                 110

Leu Lys Asn Tyr Phe Leu Thr Lys Gly Ser Arg Glu Asp Ala Val Gln
        115                 120                 125

Leu Val Ile Ile Phe Thr Asp Gly Ser Pro Asp Asn Lys Glu Ser Ala
    130                 135                 140

Met Lys Glu Val Asn Lys Leu Lys Lys Met Lys Ala Lys Phe Ala Val
145                 150                 155                 160

Ile Gly Val Gly Met Gly Ile Asn Lys Glu Phe Asn Lys Ser Leu Val
                165                 170                 175

Gly Cys Pro Leu Lys Glu Lys Lys Cys Asp Leu Tyr Ser Glu Ala Ser
            180                 185                 190
```

```
Trp Asn Glu Val Gln Asn Val Ile Ala Pro Phe Leu Lys Glu Val Cys
195 200 205

Ile Glu Val Glu Lys Val Ala His Cys Gly Ser Trp Gly Glu Trp Ser
210 215 220

Pro Cys Ser Val Thr Cys Gly Glu Gly Val Arg Thr Arg Arg Arg Glu
225 230 235 240

Val Leu His Lys Gly Cys Thr Asp His Met Thr Val Leu Cys Glu Lys
245 250 255

Pro Asn Cys Pro
260

<210> SEQ ID NO 24
<211> LENGTH: 245
<212> TYPE: PRT
<213> ORGANISM: Artificial Sequence
<220> FEATURE:
<223> OTHER INFORMATION: fragment of plasmodium relictum TRAP

<400> SEQUENCE: 24

His Glu Lys Val Asp Leu Tyr Ile Leu Met Asp Gly Ser Gly Ser Ile
1 5 10 15

Gly Tyr Asp Asn Trp Ile Ser Tyr Ala Val Pro Leu Val Tyr Asp Ile
20 25 30

Val Lys Asn Leu Asn Val Ser Asn Asp Gly Ile His Leu Tyr Leu Ser
35 40 45

Val Phe Thr His Tyr Leu Arg Glu Tyr Ile Lys Leu Gly Ser Ser Leu
50 55 60

Ser Thr Asn Arg Glu Phe Ala Leu Asn Ile Ile Glu Asn Leu Lys Asn
65 70 75 80

Lys Tyr Tyr Leu His Gly Ser Thr Asn Leu Thr Ile Ala Leu Ser Arg
85 90 95

Val Leu Gln Asp Asn Phe Ile Lys Lys Lys Gly Arg Glu Asp Ala Val
100 105 110

Gln Leu Ile Leu Ile Phe Thr Asp Gly Ala Pro Asp Asp Lys Glu Thr
115 120 125

Ala Met Gln Glu Val Val Lys Leu Lys Lys Met Asn Ala Lys Phe Ser
130 135 140

Val Ile Gly Val Gly Met Gly Ile Asn Arg Glu Phe Asn Lys Arg Leu
145 150 155 160

Val Asp Cys Ser Pro Tyr Glu Glu Lys Cys Asp Leu Tyr Ser Glu Ala
165 170 175

Ser Trp Val Asp Val Lys Asp Ile Ile Ala Pro Phe Leu Lys Lys Val
180 185 190

Cys Val Glu Ile Glu Lys Val Ala His Cys Gly Ser Trp Gly Glu Trp
195 200 205

Thr Pro Cys Ser Val Thr Cys Gly Glu Gly Ile Lys Thr Arg Lys Arg
210 215 220

Asn Ile Leu His Lys Gly Cys Ser Asp His Met Asn Ala Leu Cys Glu
225 230 235 240

Lys Pro Glu Cys Pro
245

What is claimed is:

1. A *Plasmodium falciparum* Thrombospondin-Related Anonymous Protein (TRAP) antigen that is at least 80% identical to amino acids 25-574 of SEQ ID NO:5, wherein the antigen sequence comprises one or more of the following mutations or deletions:
   (a) Mutation at Cysteine 55 to a non-cysteine amino acid;
   (b) Mutation of N-linked glycosylation sites;
   (c) Mutation of Ala-216/Asn-222 or Lys-224/Gln-78 to cysteine to create a TRAP that is stabilized in the open conformation;
   (d) Mutation of Asn-213/Ala-233, Ala-216/Phe-230, or Met-231/Gln-78 to cysteine to create a TRAP that is stabilized in the closed conformation;
   (e) Deletion of N-terminal and/or C-terminal residues to create a TRAP fragment that is stabilized in the closed conformation comprising V47-V238;
   (f) Deletion of N-terminal and/or C-terminal residues to create a TRAP fragment that is stabilized in the open conformation comprising V47-M231,
and wherein the antigen can elicit an immune response in a mammalian subject.

2. The antigen of claim 1, wherein the sequence is a mutated *P. falciparum* TRAP sequence that is at least 95% identical to SEQ ID NO:5.

3. The antigen of claim 1, wherein the mutation at Cys55 is to Glycine, Serine, or Alanine.

4. The antigen of claim 1, wherein the mutation of an N-linked glycosylation site is a mutation of N or (S/T) in the carbohydrate-encoding sequence N-X-(S/T).

5. The antigen of claim 4, wherein the mutation is N132S, S477N, and/or N483S.

6. A fusion protein comprising the antigen of claim 1 fused to one or more of an adjuvant, carrier, or protein purification sequence.

7. The fusion protein of claim 6, wherein the protein purification sequence comprises a FLAG sequence or a 6His sequence.

8. The fusion protein of claim 6, wherein the carrier comprises a hepatitis B surface protein.

9. A composition comprising one or more of the antigens or fusion proteins of claim 1.

10. A pharmaceutical composition comprising one or more of the antigens of claim 1 and a physiologically acceptable carrier.

11. The pharmaceutical composition of claim 10, further comprising an adjuvant.

12. A method of inducing an immune response in a mammal, the method comprising administering to the subject a pharmaceutical composition comprising one or more of the antigens of claim 1.

13. The method of claim 12, wherein the pharmaceutical composition further comprises an adjuvant.

* * * * *